US012770255B2

(12) United States Patent
Matsuzaki et al.

(10) Patent No.: US 12,770,255 B2
(45) Date of Patent: Oct. 20, 2026

(54) SURGERY ASSISTING SYSTEM, SURGERY ASSISTING METHOD, AND SURGERY ASSISTING PROGRAM

(71) Applicant: Jmees Inc., Kashiwa (JP)

(72) Inventors: Hiroki Matsuzaki, Kashiwa (JP); Masayasu Tanase, Kashiwa (JP); Nobuyoshi Takeshita, Kashiwa (JP)

(73) Assignee: Jmees Inc., Kashiwa (JP)

( * ) Notice: Subject to any disclaimer, the term of this patent is extended or adjusted under 35 U.S.C. 154(b) by 234 days.

(21) Appl. No.: 18/675,622

(22) Filed: May 28, 2024

(65) Prior Publication Data

US 2024/0362777 A1 Oct. 31, 2024

Related U.S. Application Data

(63) Continuation of application No. PCT/JP2022/038698, filed on Oct. 18, 2022.

(30) Foreign Application Priority Data

Nov. 26, 2021 (JP) ................................ 2021-192441

(51) Int. Cl.
*G06K 9/00* (2022.01)
*G06T 7/00* (2017.01)
(Continued)

(52) U.S. Cl.
CPC .............. *G06T 7/0012* (2013.01); *G06T 7/70* (2017.01); *G16H 20/40* (2018.01);
(Continued)

(58) Field of Classification Search
CPC .......... A61B 1/00006; A61B 1/000094; A61B 1/045; A61B 5/4848; A61B 1/043;
(Continued)

(56) References Cited

U.S. PATENT DOCUMENTS 10,299,864 B1 * 5/2019 Yu ............................ G06T 7/70
10,383,694 B1 * 8/2019 Venkataraman ...... G06T 7/0012
(Continued)

FOREIGN PATENT DOCUMENTS

JP 2008-307225 12/2008
JP 2020-156860 10/2020
(Continued)

OTHER PUBLICATIONS

Extended European Search Report dated Apr. 29, 2025, from counterpart European Patent Application No. 22898276.5.
(Continued)

*Primary Examiner* — Alex Kok S Liew
(74) *Attorney, Agent, or Firm* — DLA Piper LLP (US)

(57) ABSTRACT

A surgery assisting system includes an image acquisition unit capturing endoscope images, a surgical technique selection reception unit for selecting a surgical technique, an organ area estimation unit utilizing an organ area estimation model to predict the position and range of a potentially damaged organ based on the selected surgical technique and captured image, and an estimated area display unit overlaying the predicted organ damage information onto the captured image. This system enhances surgical planning by providing real-time visualization of potential organ damage areas, aiding surgeons in performing procedures with increased precision and safety.

18 Claims, 11 Drawing Sheets

(51) Int. Cl.
*G06T 7/70* (2017.01)
*G16H 20/40* (2018.01)

(52) U.S. Cl.
CPC ............... *G06T 2207/10068* (2013.01); *G06T 2207/20081* (2013.01); *G06T 2207/30101* (2013.01)

(58) Field of Classification Search
CPC ... A61B 5/0071; A61B 1/00; A61B 1/000095; A61B 1/00055; A61B 1/00059; A61K 35/407; A61K 49/006; A61K 47/14; A61K 47/44; A61K 9/1075; A61K 47/6957; G06F 3/011; G06F 18/28; G06N 20/20; G06N 5/01; G06N 7/01
See application file for complete search history.

(56) References Cited

U.S. PATENT DOCUMENTS

| | | | | |
|---|---|---|---|---|
| 2004/0254566 | A1* | 12/2004 | Plicchi | A61B 34/37 606/1 |
| 2008/0312499 | A1 | 12/2008 | Handa et al. | |
| 2016/0199147 | A1* | 7/2016 | Shin | A61B 90/37 600/411 |
| 2017/0007350 | A1* | 1/2017 | Popovic | A61B 1/00165 |
| 2020/0085287 | A1* | 3/2020 | Lawrenson | A61B 1/0676 |
| 2020/0297422 | A1 | 9/2020 | Gocho et al. | |
| 2021/0287395 | A1 | 9/2021 | Ishikake et al. | |

FOREIGN PATENT DOCUMENTS

| | | |
|---|---|---|
| JP | 7081862 | 6/2022 |
| WO | 2019/116593 | 6/2019 |
| WO | 2020/110278 | 6/2020 |

OTHER PUBLICATIONS

International Search Report dated Dec. 13, 2022, of counterpart International Application No. PCT/JP2022/038698, along with an English translation.
Office Action dated Mar. 22, 2022, of counterpart Japanese Application No. 2021-192441, along with English translation.
Office Action dated Jul. 26, 2022, of counterpart Japanese Application No. 2022-082189, along with an English translation.
Office Action dated Jun. 17, 2026, from counterpart European Application No. 22898276.5.

* cited by examiner

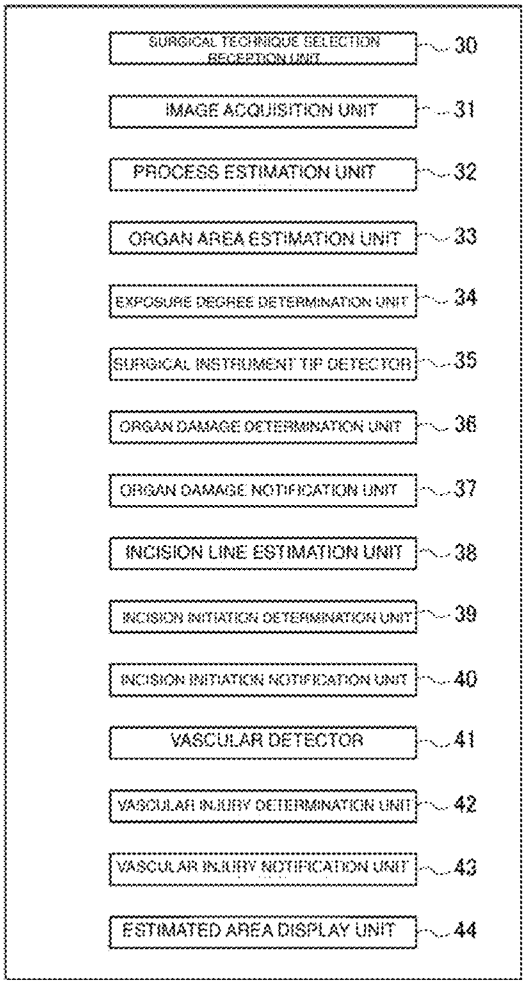

FIG. 2

| SURGICAL TECHNIQUE NAME | SIGMOIDECTOMY |
|---|---|
| PROCESS 1 | RECTAL HIND CAVITY PROCESSING |
| PROCESS 2 | INNER MOBILIZATION BEFORE VASCULAR PROCESSING |
| PROCESS 3 | VASCULAR PROCESSING |
| PROCESS 4 | INNER MOBILIZATION AFTER VASCULAR PROCESSING |
| PROCESS 5 | OUTER MOBILIZATION |
| PROCESS 6 | RECTAL CIRCUMFERENCE PEELING |
| PROCESS 7 | RECTAL MESENTERY PROCESSING |
| PROCESS 8 | DISSECTION/ANASTOMOSIS |
| PROCESS 9 | INFERIOR MESENTERIC VEIN (LEFT COLIC ARTERY) PROCESSING |

FIG. 3

SURGERY ASSISTING SYSTEM, SURGERY ASSISTING METHOD, AND SURGERY ASSISTING PROGRAM

CROSS-REFERENCE TO RELATED APPLICATIONS

This application is a continuation application of International Application No. PCT/JP2022/038698, filed on Oct. 18, 2022, which claims priority of Japanese (JP) Patent Application No. 2021-192441, filed on Nov. 26, 2021, the contents of each of which are hereby incorporated by reference in its entirety.

BACKGROUND

This disclosure relates to a surgery assisting system, a surgery assisting method, and a surgery assisting program. More specifically, this disclosure relates to a surgery assisting system, a surgery assisting method, and a surgery assisting program that assist the surgeon in recognizing organs during surgery using an endoscope.

The endoscopic procedure has been performed in a considerable number of facilities in recent years. Surgeries using endoscopes include endoscopic surgery in which an endoscope is inserted into the digestive organs, for example, through the mouth, nose, or anus; laparoscopic surgery in which an endoscope is inserted into the abdominal cavity; thoracoscopic surgery in which an endoscope is inserted into the thoracic cavity; and arthroscopic surgery in which an endoscope is inserted into an arthrosis.

In the laparoscopic surgery, for example, several incisions with a size of 5 to 12 mm are formed in the abdomen, a laparoscope (a type of endoscope), forceps, and electrocautery are inserted into the abdominal cavity through the incisions, and images captured by the laparoscope are displayed on a monitor to perform operations.

The advantages of laparoscopic surgery include: small and inconspicuous wounds caused by incisions, which are cosmetically superior; less postoperative pain and quicker recovery than abdominal operation; lower risk of infection; and less blood loss.

In contrast, endoscopic surgery including laparoscopic surgery has the disadvantages that it needs time and experience to master the technique since the field of vision of the surgeon is limited and the surgeon cannot directly touch organs, for example, and therefore great differences may be recognized in technique among surgeons and facilities.

Therefore, with the aim of reducing the above disadvantages of surgery using the endoscope, an endoscopic system was proposed to enable wide-area observation of the entire treatment area to be operated (see Japanese Laid-Open Patent Publication No. 2008-307225). The technology disclosed in JP2008-307225A claims to be able to ensure a wide intraoperative field of view by using a small camera that is placed in the body cavity along with an endoscope.

However, the technique disclosed in JP2008-307225A needs the placement of the small camera in an appropriate position in the body cavity of the subject prior to the surgery and the continued placement of the small camera in an appropriate position during the surgery. This may increase the burden on the subject since it takes a certain amount of time to set up the small camera.

In addition, the small camera needs to be removed from the body cavity of the subject after the surgery, which may also increase the burden on the subject.

It could therefore be helpful to provide a surgery assisting system, a surgery assisting method, and a surgery assisting program that are capable of providing surgical assist to a surgeon by superimposing a certain organ that the surgeon should recognize during the operation on an image captured by an endoscope without increasing the burden on the subject undergoing the surgery.

SUMMARY

We thus provide:

A surgery assisting system according to the first aspect includes: an image acquisition unit that acquires an image captured by an endoscope; an organ area estimation unit that inputs the image acquired by the image acquisition unit into an organ area estimation model that has learned in advance a relationship between the image captured during the surgery, and a position and range of a certain organ in the image to estimate the position and range of the certain organ in the image acquired by the image acquisition unit; and an estimated area display unit that superimposes and displays information indicating the position and range of the certain organ estimated by the organ area estimation unit on the image acquired by the image acquisition unit.

In the second aspect, in the surgery assisting system according to the first aspect, the organ area estimation model may correspond to a model that has learned in advance the relationship among identification information indicating a surgical technique of the surgery, the image captured during the surgery, and a position and range of a certain organ associated with the surgical technique in the image. The system may further include a surgical technique selection reception unit that accepts a selection of a surgical technique of the surgery, and the organ region estimation unit may estimate the position and range of the certain organ in the image acquired by the image acquisition unit by inputting the image acquired by the image acquisition unit and the identification information indicating the surgical technique accepted by the surgical technique selection reception unit into the organ area estimation model.

In the surgery assisting system according to the second aspect, the third aspect may include a process estimation unit that estimates a process of a surgical technique in the image acquired by the image acquisition unit by inputting the image acquired by the image acquisition unit and identification information indicating the surgical technique accepted by the surgical technique selection reception unit into a process classification model that has learned in advance the relationship between each of a series of processes whose steps from a start to end of the surgical technique in the surgery are classified for each content and carried out sequentially, and the image captured during the surgery, the organ area estimation model may correspond to a model that has learned the relationship among the identification information indicating the surgical technique in the surgery, the identification information indicating the process of the surgical technique, the image captured during the surgery, and the position and range of a certain organ associated with the process of the surgical technique in the image, and the organ area estimation unit may estimate the position and range of the certain organ in the image acquired by the image acquisition unit by inputting the image acquired by the image acquisition unit, the identification information indicating the surgical technique accepted by the surgical technique selection reception unit, and the identification information indicating the process estimated by the process estimation unit into the organ area estimation model.

In the surgery assisting system according to the third aspect, the fourth aspect may include an incision line estimation unit that inputs the image acquired by the image acquisition unit, the identification information indicating the surgical technique accepted by the surgical technique selection reception unit, and the identification information indicating the process estimated by the process estimation unit into the incision line estimation model that has learned in advance the relationship among the organ for the process of the surgical technique of the surgery, the image before the incision at the incision point by the surgery, and the image acquired by annotating the image before the incision with the trajectory of the tip portion of the surgical instrument at the time of the incision to estimate the position and range of the incision line through which the tip portion of the surgical instrument should pass at the time of incision in the image acquired by the image acquisition unit, and the estimated area display unit may superimpose and display the information indicating the incision line estimated by the incision line estimation unit on the image acquired by the image acquisition unit.

In the surgery assisting system according to the fourth aspect, the fifth aspect may include: a surgical instrument tip detector that detects a position of a tip portion of a surgical instrument in the image acquired by the image acquisition unit using a surgical instrument detection model that has learned in advance the shape of the tip portion of the surgical instrument; an incision initiation determination unit that determines whether the position of the tip portion detected by the surgical instrument tip detector has reached the incision line estimated by the incision line estimation unit; and an incision initiation notification unit that notifies the surgeon of the possibility of the incision initiation when the incision initiation determination unit determines that the position of the tip portion has reached the estimated incision line.

In the surgery assisting system according to any one of the first through third aspects, the sixth aspect may include: a surgical instrument tip detector that detects a position of a tip portion of a surgical instrument in the image acquired by the image acquisition unit using a surgical instrument detection model that has learned in advance the shape of the tip portion of the surgical instrument; an organ damage determination unit that determines whether the position of the tip portion detected by the surgical instrument tip detector has reached the position and range of the certain organ estimated by the organ area estimation unit; and an organ damage notification unit that notifies the surgeon of the possibility of the organ damage when the organ damage determination unit determines that the position of the tip portion has reached the estimated position and range.

In the surgery assisting system according to any one of the first through third aspects, the seventh aspect may include: a surgical instrument tip detector that detects a position of the tip portion of the surgical instrument in the image acquired by the image acquisition unit using a surgical instrument detection model that has learned in advance the shape of the tip portion of the surgical instrument; a vascular detector that detects the position and range of the blood vessel in the image acquired by the image acquisition unit; a vascular injury determination unit that determines whether the position of the tip portion detected by the surgical instrument detector has reached the blood vessel detected by the vascular detector; and a vascular injury notification unit that notifies the surgeon of the possibility of vascular injury if the vascular injury determination unit determines that the position of the tip portion has reached the blood vessel.

In the eighth aspect, in the surgery assisting system according to any one of the first to seventh aspects, when the organ area estimation unit estimates the position and range of a plurality of certain organs in the image acquired by the image acquisition unit, the estimated area display unit may superimpose and display the information indicating the certain organs estimated by the organ area estimation unit on the image acquired by the image acquisition unit in different display forms, respectively.

In the ninth aspect, in the surgery assisting system according to any one of the first to eighth aspects, when the organ to be learned has automaticity, the organ area estimation model may learn in advance the form of movement associated with the automaticity, and when the certain organ estimated by the organ area estimation unit has automaticity, the estimated area display unit may display the information indicating the certain organ estimated by the organ area estimation unit by superimposing the information indicating the certain organ on the image acquired by the image acquisition unit by highlighting the information in a predetermined manner.

In the surgery assisting system according to any one of the first through the ninth aspects, the tenth aspect may include an exposure degree determination unit that determines the exposure degree of the certain organ by comparing the position and range of the certain organ estimated by the organ area estimation unit with the image acquired by the image acquisition unit, and the estimated area display unit may change the display form of information indicating the certain organ estimated by the organ area estimation unit in accordance with the exposure degree determined by the exposure degree determination unit.

In the eleventh aspect, in the surgery assisting system according to any one of the first to tenth aspects, the image acquisition unit may acquire a plurality of consecutive images, and the organ area estimation unit may estimate the trajectory of the position and range of the certain organ by inputting the consecutive images acquired by the image acquisition unit into the organ area estimation model.

In the twelfth aspect, in the surgery assisting system according to any one of the first to eleventh aspects, the image acquisition unit may acquire at least one of the image captured by the computed tomography before the surgery and image captured by the magnetic resonance imaging before the surgery along with the image captured by the endoscope, the organ area estimation unit may estimate the position and range of a certain organ by inputting the image acquired by the image acquisition unit into an organ area estimation model, and the estimated area display unit may superimpose and display the information indicating the position and range of the certain organ estimated by the organ area estimation unit on at least one of the image captured by the computed tomography before the surgery and the image captured by the magnetic resonance imaging before the surgery, which are acquired by the image acquisition unit.

In the thirteenth aspect, in the surgery assisting system according to any one of the first to twelfth aspects, the certain organ may be directed to an organ with a high probability of being damaged during the surgery.

In the fourteenth aspect, in the surgery assisting system according to the eighth aspect, when the endoscope corresponds to a laparoscope and the organ area estimation unit estimates the position and range of two adjacent organs by inputting the image acquired by the image acquisition unit into the organ area estimation model, the estimation area display unit may superimpose and display, from among the information indicating the position and range of one of the two adjacent organs, the portion closer to the position and range of the other of the two adjacent organs on the image acquired by the image acquisition unit.

A surgery assisting method according to the fifteenth aspect causes a computer used in a surgery assisting system to perform: an image acquisition step of acquiring an image captured by an endoscope; an organ area estimation step of inputting the image acquired in the image acquisition step into an organ area estimation model that has learned in advance a relationship between the image captured during the surgery, and a position and range of a certain organ in the image to estimate the position and range of the certain organ in the image acquired in the image acquisition step; and an estimated area display step of superimposing and displaying information indicating the position and range of the certain organ estimated in the organ area estimation step on the image acquired in the image acquisition step.

A surgery assisting program according to the sixteenth aspect causes a computer used in a surgery assisting system to embody: an image acquisition function that acquires an image captured by an endoscope; an organ area estimation function that inputs the image acquired by the image acquisition function into an organ area estimation model that has learned in advance a relationship between the image captured during the surgery, and a position and range of a certain organ in the image to estimate the position and range of the certain organ in the image acquired by the image acquisition function; and an estimated area display function that superimposes and displays information indicating the position and range of the certain organ estimated by the organ area estimation function on the image acquired by the image acquisition function.

The surgery assisting system according to the present disclosure, for example, includes: an image acquisition unit that acquires an image captured by an endoscope; an organ area estimation unit that inputs the image acquired by the image acquisition unit into an organ area estimation model that has learned in advance a relationship between the image captured during the surgery, and a position and range of a certain organ in the image to estimate the position and range of the certain organ in the image acquired by the image acquisition unit; and an estimated area display unit that superimposes and displays information indicating the position and range of the certain organ estimated by the organ area estimation unit on the image acquired by the image acquisition unit. This can provide surgical assist to a surgeon by superimposing and displaying the certain organ on the image captured by the endoscope without increasing the burden on a subject undergoing the surgery.

In some aspects, disclosed herein is a non-transitory computer readable medium storing therein a surgery assisting program that causes a computer used in a surgery assisting system to embody: an image acquisition function that acquires an image captured by an endoscope; a surgical technique selection reception function that accepts a selection of a surgical technique of a surgery; an organ area estimation function that inputs the image acquired by the image acquisition function and identification information indicating the surgical technique accepted by the surgical technique selection reception function into an organ area estimation model that has learned in advance a relationship among identification information indicating the surgical technique of the surgery, the image captured by the endoscope during the surgery, and a position and range of an organ that is likely to be damaged during the surgery associated with the surgical technique in the image to estimate the position and range of the organ that is likely to be damaged during the surgery in the image acquired by the image acquisition function; and an estimated area display function that superimposes and displays information indicating the position and range of the organ that is likely to be damaged during the surgery estimated by the organ area estimation function on the image acquired by the image acquisition unit.

BRIEF DESCRIPTION OF THE DRAWINGS

Features, advantages, and technical and industrial significance of exemplary embodiments of the disclosure will be described below with reference to the accompanying drawings, in which like numerals denote like elements, and wherein:

FIG. 2 is a block diagram illustrating an example of a functional configuration for the surgery assisting system, FIG. 3 is a table used to illustrate an example of a surgical process for the surgery assisting system.

DETAILED DESCRIPTION

With reference to FIGS. 1 to 10, a surgery assisting system 10 will be described.

The surgery assisting system 10 is directed to an electronic computer represented by a personal computer, notebook PC, and tablet computer, for example, which is connected to external devices such as an endoscope system 14 described below, and inputs and outputs data to and from the external devices. The surgery assisting system 10 is capable of immediately performing image analysis on the moving or still images captured by the endoscope system 14 and outputting the results of the image analysis along with the relevant images captured by the endoscope of the endoscope system 14 to a monitor 12. The surgery assisting system 10 exists as a stand-alone device is shown, but it is not limited to this instance, and the surgery assisting system 10 may be modularized and incorporated as part of other electronic computers.

The endoscope system 14 is configured by an endoscope, forceps, surgical energy device, trocar, video processor, and endoscopic display.

The endoscope is inserted into the body to view the inside, and is also referred to as a scope. It is also referred to as a laparoscope, thoracoscope, neuroendoscope, otolaryngological scope, bronchoscope, upper digestive endoscope, biliary endoscope, duodenoscope, colonoscope, enteroscope, cystourethroscope, or arthroscope depending on the portion of the body in which it is used. This disclosure describes an example in which the surgery assisting system 10 is connected to an endoscope system 14 used for laparoscopic surgery, but the surgery assisting system 10 may also be connected to an endoscope system 14 used for other portions of the body, such as thoracoscope.

Forceps are a type of surgical instrument and may include grasping forceps for grasping organs such as viscera, dissecting forceps for peeling off tissue, and scissors forceps for cutting and excising portions of lesions of the body, for example.

Surgical energy devices are directed to surgical instruments that use the force of energy to cutting and excising tissue and stop bleeding. The energy may mainly include high-frequency current, which is excellent for hemostasis, and ultrasonic vibration, which is excellent for cutting and excising tissue.

The trocar includes a needle and tube, which is used to drain or vent the thoracic or abdominal cavity.

The video processor performs noise suppression processing, conversion processing to video signals, and white balance processing, for example, on the electrical signals from the endoscope, and outputs the video signals from the endoscope to the endoscope display and surgery assisting system 10.

Mechanical Configuration of the Surgery Assisting System 10

Figure 1:
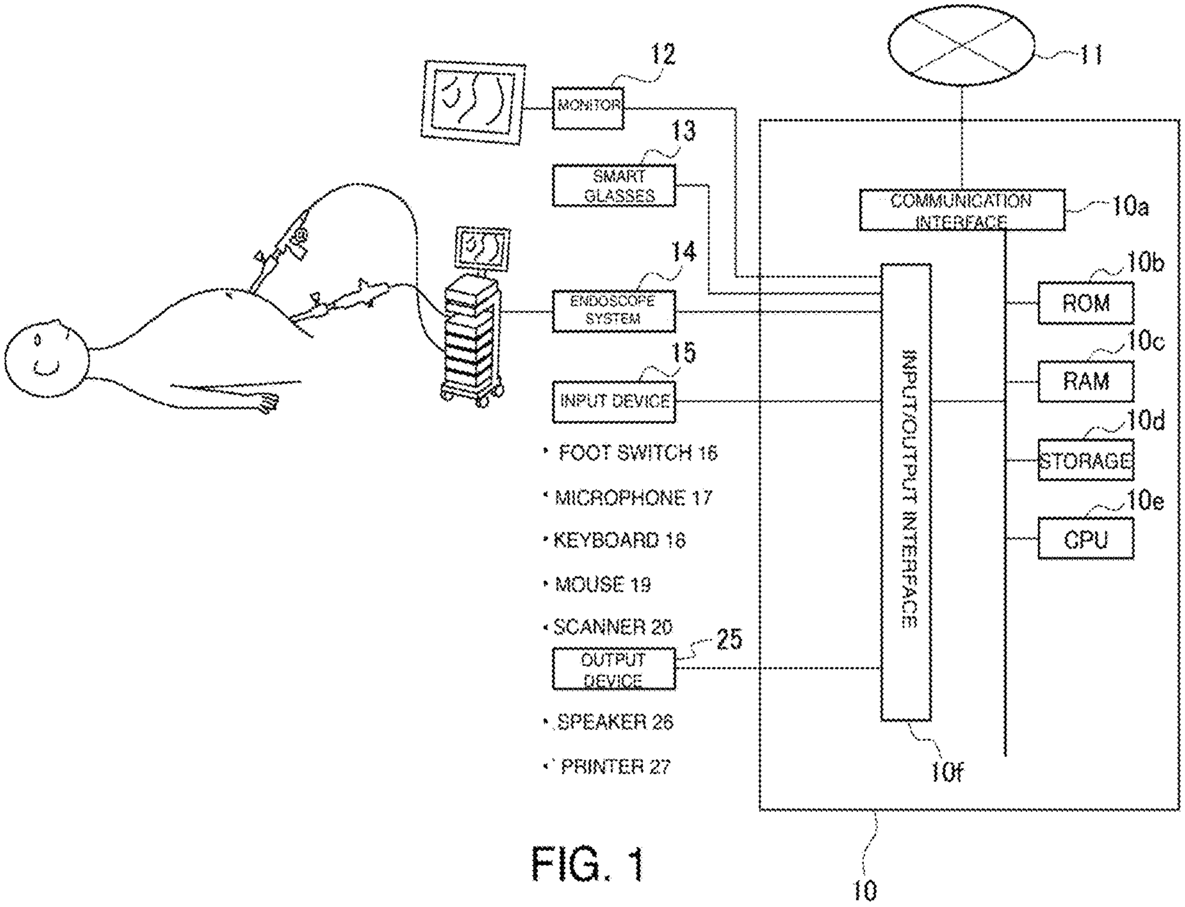
FIG. 1 is a block diagram illustrating an example of a mechanical configuration for a surgery assisting system.

With reference to FIG. 1, an example of a mechanical configuration of the surgery assisting system 10 will be described. FIG. 1 is a block diagram illustrating an example of a mechanical configuration of the surgery assisting system 10.

The surgery assisting system 10 may include a communication interface 10*a*, read only memory (ROM) 10*b*, random access memory (RAM) 10*c*, storage 10*d*, central processing unit (CPU) 10*e*, and input/output interface 10*f*, for example. The surgery assisting system 10 may also include, as its external devices, a monitor 12, smart glasses 13, endoscope system 14, input device 15 and output device 25.

The storage 10*d* may be used as a storage device, and stores the surgery assisting program, various applications, and various data used by the applications, which are needed for the operation of the surgery assisting system 10, as described below. Further, the storage 10*d* stores in advance the various learned models described below that have been generated by machine learning for various applications.

The input/output interface 10*f* transmits and receives data and other data to and from external devices: monitor 12, smart glasses 13, endoscope system 14, input device 15, and output device 25. The input device 15 may include a foot switch 16, microphone 17, keyboard 18, mouse 19, and scanner 20, for example, and the output device 25 may include a speaker 26, and printer 27, for example. That is, these are peripheral devices of the surgery assisting system 10.

The communication interface 10*a* enables data, for example, to be transmitted to and received from the network 11, and may be connected to information processing terminals such as an instructor or leader that remotely provides instructions and guidance.

The surgery assisting system 10 stores a surgery assisting program needed for operation in the ROM 10*b* or storage 10*d*, and reads the surgery assisting program into the main memory configured by the RAM 10*c*, for example. The CPU 10*e* accesses the main memory that contains the surgery assisting program, executes the surgery assisting program, and provides various functional units as described below.

The smart glasses 13 are worn on the head by a surgeon or other person and include a monitor and a microphone that supply visual and auditory information to the surgeon, a gyro sensor that detects the motion and posture of the surgeon, and a microphone that collects the sound of the voice of the surgeon. When the surgeon shakes his/her head, the gyro-sensor detects the motion of the surgeon and may give command signals to the surgery assisting system 10. The surgeon may also give command signals to the surgery assisting system 10 by emitting a certain voice to the microphone. The smart glasses 13 may be used as a substitute for a head mounted display (HMD).

The foot switch 16 corresponds to a switch operated by the foot of the surgeon or other person and is capable of providing command signals to the surgery assisting system 10.

Functional Configuration of the Surgery Assisting System 10

With reference to FIG. 2, an example of a functional configuration of the surgery assisting system 10 will be described. FIG. 2 is a block diagram illustrating an example of a functional configuration of the surgery assisting system 10.

The surgery assisting system 10 stores the surgery assisting program needed for operation in the ROM 10*b* or the storage 10*d*, and reads the surgery assisting program into the main memory configured by the RAM 10*c*, for example. The CPU 10*e* executes the surgery assisting program by accessing the main memory that contains the surgery assisting program.

By executing the surgery assisting program, the surgical operation support system 10 may include the following functional units in the CPU 10*e*: surgical technique selection reception unit 30, image acquisition unit 31, process estimation unit 32, organ area estimation unit 33, exposure degree determination unit 34, surgical tool tip detector 35, organ damage determination unit 36, organ damage notification unit 37, incision line estimation unit 38, incision initiation determination unit 39, incision initiation notification unit 40, vascular detector 41, vascular damage determination unit 42, vascular damage notification unit 43, and estimated area display unit 44, for example.

Surgical Technique Selection Reception Unit

The surgical technique selection reception unit 30 receives selection of a surgical technique.

The user of the surgery assisting system 10, such as a surgeon, selects a surgical technique to be performed from among the surgical techniques registered in advance in the surgery assisting system 10. As an example, the surgeon may use a pointing device such as a mouse or voice input function to select a surgical technique from a menu of the surgical techniques displayed on the monitor 12 or smart glasses 13. The surgical technique selection reception unit 30 accepts the selection of the surgeon or other person for the surgical technique for the relevant operation before the operation begins. The surgical technique can be changed in the middle of the surgery, and the surgical technique selection reception unit 30 is capable of accepting the selection of another surgical technique in the middle of the surgery, and the surgery assisting system 10 performs subsequent processing using the identification information of the other surgical technique accepted in the middle of the surgery.

Image Acquisition Unit

The image acquisition unit 31 acquires images captured by the endoscope.

Specifically, the image acquisition unit 31 acquires video signals of moving or still images captured by the endoscope by acquiring output signals from the video processor of the endoscope system 14. The image acquisition unit 31 is also capable of acquiring images captured by computed tomography (CT) and magnetic resonance imaging (MRI) devices, which are not shown. The endoscope system 14 is capable of acquiring images captured by the computed tomography (CT) device and the magnetic resonance imaging (MRI) device, but the computed tomography (CT) device and the MRI device are not essential to this disclosure.

Process Estimation Unit

The process estimation unit 32 estimates the process of the surgical technique in the image acquired by the image acquisition unit 31 by inputting the image acquired by the image acquisition unit 31 and the identification information indicating the surgical technique accepted by the surgical technique selection reception unit 30 into a process classification model that classifies a series of processes of the surgical technique of the operation from start to end for each content and learns the relationship between each process in the series of processes sequentially performed and the images captured during the surgery.

The process estimation unit 32 inputs the image acquired by the image acquisition unit 31 into the process classification model to perform scene recognition of the image and estimate the process related to the image.

With reference to FIG. 3, a configuration of the surgical technique will be described. FIG. 3 is a table illustrating an example of surgical processes for the surgery assisting system 10. Sigmoidectomy will be described as an example of a surgical technique. The sigmoidectomy is classified into nine processes from start to end. The nine processes may include: process 1 "rectal hind cavity processing," process 2 "inner mobilization before vascular processing," process 3 "vascular processing," process 4 "inner mobilization after vascular processing," process 5 "outer mobilization," process 6 "rectal circumference peeling," process 7 "rectal mesentery processing," process 8 "dissection/anastomosis," and process 9 "inferior mesenteric vein (left colic artery) processing. The surgical techniques are classified into processes, allowing the surgical procedures, accuracy, needed time, and physical condition of the subject to be managed for each process. This is useful for efficient overall surgical management as well as for learning and training surgical techniques.

The process classification model is directed to a model that has learned in advance the correspondence between the images captured for each surgical process and the identification information of the process of the surgical technique in the images, and is generated by machine learning and stored in advance in the storage **10*d* of the surgery assisting system 10**.

Organ Area Estimation Unit

The organ area estimation unit 33 inputs the images acquired by the image acquisition unit 31 into the organ area estimation model, which has learned in advance the relationship between the images captured during surgery and the position and range of a certain organ in the images to estimates the position and range of the certain organ in the images acquired by the image acquisition unit 31.

The organs are directed to viscera, muscles, ligaments, tendons, blood vessels, nerves, ureters, and bones, for example, correspond to the units that configure the human body, and are a collection of tissues that control certain functions.

The organ area estimation model learns in advance using teacher data in which the certain organ is annotated in an image captured during surgery, the relationship with the position and range of the certain organ in the image, but the model is not limited to this. The organ area estimation unit 33 may estimate the position and range of the certain region in the image acquired by the image acquisition unit 31 by using teacher data in which the region most likely to be damaged during surgery independent of the organ is annotated and inputting the image acquired by the image acquisition unit 31 into a model that has learned in advance the relationship with the position and range of the certain region in the image. The certain region may correspond to, for example, a greater area that is present across multiple organs and is subject to damage during surgery, or a portion of an organ that is subject to damage during surgery.

The organ area estimation unit 33 inputs images captured by the endoscope of the endoscope system 14 into the organ area estimation model to estimate the position and range of the certain organ in the images in real time (immediately). The estimation results of the organ area estimation unit 33 are superimposed on the images captured by the endoscope in real time (immediately) and displayed on the monitor 12 by the estimated area display unit 44 described below. This allows the surgeon to check the estimation results displayed on the monitor 12 during the surgery, and perform the surgery while paying attention to the position and range of the certain organ.

The organ to be estimated by the organ area estimation unit 33 may be correspond to the organ with a high probability of being damaged during the surgery. The organ area estimation model is directed to a model that has learned in advance the relationship between the images captured during the surgery and the position and range of the organs with a high probability of being damaged during the surgery in the images. The organ area estimation unit 33 inputs the images acquired by the image acquisition unit 31 into the relevant organ area estimation model to estimate the position and range of the organs with a high probability of being damaged during the surgery in the images acquired by the image acquisition unit 31. The surgery assisting system 10 is capable of estimating the position and area of the organs with a high probability of being damaged during the surgery, and indicating the position and area of the organs in real time (immediately) in the images acquired by the image acquisition unit 31, thus providing intraoperative assistance to the surgeon.

The organ area estimation model may correspond to a model that has learned in advance the relationship among the identification information indicating the surgical technique in the operation, the image captured during the surgery, and the position and range of the certain organ associated with the surgical technique in the image. The organ area estimation unit 33 inputs the image acquired by the image acquisition unit 31 and the identification information indicating the surgical technique accepted by the surgical technique selection reception unit 30 into the organ area estimation model, and estimates the position and range of the certain organ in the image acquired by the image acquisition unit 31.

When the certain organ corresponds to an organ with a high probability of being damaged during the surgery, the organ area estimation model may correspond to a model that has learned in advance the relationship among the identification information indicating the surgical technique of the operation, the image captured during the surgery, and the position and range of the organ with a high probability of being damaged during the surgery using the surgical technique in the image. The organ area estimation unit 33 inputs the image acquired by the image acquisition unit 31 and the identification information indicating the surgical technique accepted by the surgical technique selection reception unit 30 into the organ area estimation model to estimate the position and range of organs with a high probability of being damaged during the surgery using the surgical technique in the image acquired by the image acquisition unit 31.

For example, when the surgical technique is a total hysterectomy and the organs with a high probability of being damaged during the surgery of the surgical technique are bladder, rectum, intestinal tract, and ureter, then the organ area estimation unit 33 inputs the image acquired by the image acquisition unit 31 and the identification information indicating a total hysterectomy accepted by the surgical technique selection reception unit 30 into the associated organ area estimation model to estimate the position and range of the bladder, rectum, intestinal tract, and ureter in the image acquired by the image acquisition unit 31. The organ area estimation unit 33 improves the accuracy of estimating the position and range of the organ to be estimated since the identification of the surgical technique narrows down the organs to be estimated.

The organ area estimation model may correspond to a model that has learned the relationship among the identification information indicating the surgical technique in the operation, the identification information indicating the process of the surgical technique, the image captured during the surgery, and the position and range of the certain organ associated with the process of the surgical technique in the image. The organ area estimation unit 33 inputs the image acquired by the image acquisition unit 31, the identification information indicating the surgical technique accepted by the surgical technique selection reception unit 30, and the identification information indicating the process estimated by the process estimation unit 32 into the organ area estimation model to estimate the position and range of the certain organ in the image acquired by the image acquisition unit 31.

When the certain organ corresponds to an organ with a high probability of being damaged during the surgery, the organ area estimation model may correspond to a model that has learned in advance the relationship among the identification information indicating the surgical technique of the operation, the identification information indicating the process of the surgical technique, the image captured during the surgery, and the position and range of the organ with a high probability of being damaged during the surgery using the surgical technique in the image. The organ area estimation unit 33 inputs the image acquired by the image acquisition unit 31, the identification information indicating the surgical technique accepted by the surgical technique selection reception unit 30, and the identification information indicating the process estimated by the process estimation unit 32 into the organ area estimation model to estimate the position and range of the organs with a high probability of being damaged during the surgery by the process in the image acquired by the image acquisition unit 31.

For example, when the surgical technique corresponds to sigmoidectomy, the process corresponds to process 6 "rectal circumference peeling," and the organs with a high probability of being damaged during the surgery of the process correspond to small intestine, ileum, and superior rectal artery, the organ area estimation unit 33 inputs the image acquired by the image acquisition unit 31, the identification information indicating the sigmoidectomy accepted by the surgical technique selection reception unit 30, and the identification information indicating process 6 "rectal circumference peeling" into the organ area estimation model, and estimates the position and range of the small intestine, ileum, and superior rectal artery in the image acquired by the image acquisition unit 31. Since the organ area estimation unit 33 narrows down the organs to be estimated by identifying the process in addition to the identification of the surgical technique, the estimation accuracy of the position and range of the organ to be estimated is improved.

Surgical Instrument Tip Detector

The surgical instrument tip detector 35 detects the position of the tip portion of the surgical instrument in the image acquired by the image acquisition unit 31 using the surgical instrument detection model that has learned in advance the shape of the tip portion of the surgical instrument.

The surgical instrument tip detector 35 detects the position of the tip portion of the surgical instrument in the image using a known 3D shape recognition method. For example, to recognize the shape of a surgical instrument as a 3D object, a learning model is generated by preparing a large number of images of the appearance of the surgical instrument used in the surgery captured from various angles, and causing a surgical instrument detection model to perform machine learning on these images as a group of multi-viewpoint images of the surgical instrument as a 3D object. The surgical instrument tip detector 35 detects the position of the tip portion of the surgical instrument in the image by inputting the image acquired by the image acquisition unit 31 into the surgical instrument detection model obtained by the machine learning.

The surgical instrument tip detector 35 may use a template corresponding to each surgical instrument and perform pattern matching to detect a surgical instrument based on whether a portion of the image acquired by the image acquisition unit 31 has a predetermined degree of similarity in relation to the template.

Figure 4:
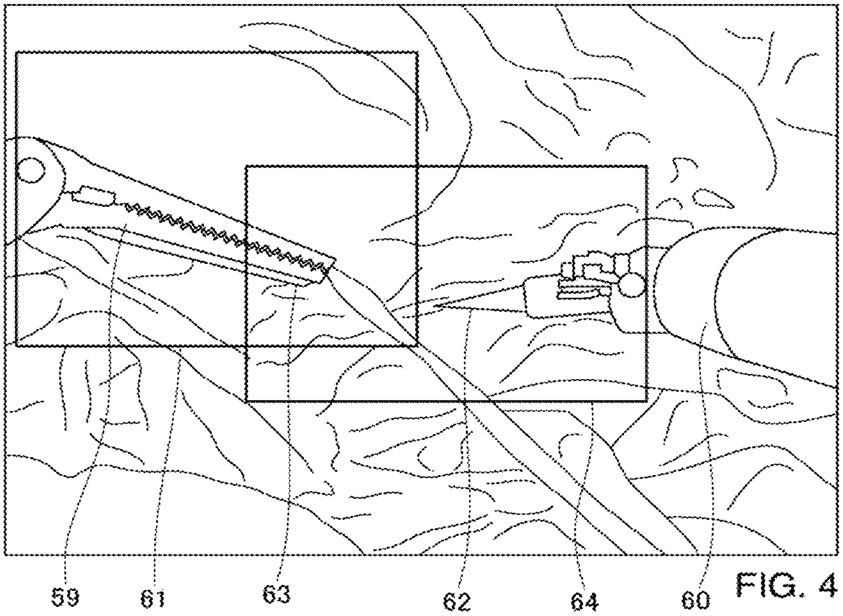
FIG. 4 is a diagram illustrating an example of a position of a distal end of a surgical instrument for the surgery assisting system, detected and superimposed on an image captured by an endoscope.

With reference to FIG. 4, the detection of the position of the tip portion of the surgical instrument in the surgical instrument tip detector 35 will be described. FIG. 4 is a diagram illustrating an example of the position of the tip portion of the surgical instrument for the surgery assisting system 10, detected and superimposed on the image captured by the endoscope.

The image shown in FIG. 4 includes two surgical instruments (first surgical instrument 59 and second surgical instrument 60). The surgical instrument tip detector 35 encloses the first surgical instrument 49 and second surgical instrument 50 in the image acquired by the image acquisition unit 31 in the first bounding box 61 and second bounding box 62. Next, the surgical instrument tip detector 35 detects the tip portion in the first bounding box 61 and second bounding box 62, and gives a first highlight 63 and a second highlight 64 on the edge portion of the tip portion. The estimated area display unit 44 superimposes the first bounding box 61, second bounding box 62, first highlight 63, and second highlight 64 on the image acquired by the image acquisition unit 31 to indicate the tip position of the surgical instrument to the surgeon.

The surgical instrument tip detector 35 is used in the organ damage determination mode, incision initiation determination mode, and vascular damage determination mode of the surgery assisting system 10 as described below.

Organ Damage Determination Mode

The organ damage determination mode of the surgery assisting system 10 detects when an organ is damaged by a surgical instrument during the surgery and notifies that to the surgeon or other person.

The organ damage determination unit 36 determines whether the position of the tip portion detected by the surgical instrument tip detector 35 has reached the position and range of a certain organ as estimated by the organ area estimation unit 33.

The organ damage notification unit 37 notifies the surgeon of the possibility of organ damage when the organ damage determination unit 36 determines that the tip portion has reached the position and range. The method of notification by the organ damage notification unit 37 may include the display of a predetermined notification screen on the monitor 12 and smart glasses 13, and the sounding of a predetermined alarm tone by the smart glasses 13 and speaker 26.

Incision Initiation Determination Mode

The incision initiation determination mode of the surgery assisting system 10 detects the initiation of the actual incision by the surgical instrument and notifies the surgeon and others of it when the surgeon incises an organ during surgery.

The incision line estimation unit 38 inputs the image acquired by the image acquisition unit 31, the identification information indicating the surgical technique accepted by the surgical technique selection reception unit 30, and the identification information indicating the process estimated by the process estimation unit 32 into the incision line estimation model that has learned in advance the relationship among the organ for the process of the surgical technique of the operation, the image before the incision at the incision point by the surgery, and the image acquired by annotating the image before the incision with the trajectory of the tip portion of the surgical instrument at the time of the incision to estimate the position and range of the incision line that the tip portion of the surgical instrument should pass through at the time of incision in the image acquired by the image acquisition unit 31.

The estimated area display unit 44 superimposes the information indicating the incision line estimated by the incision line estimation unit 38 on the image acquired by the image acquisition unit 31.

This allows the surgeon to recognize where the tip portion of the surgical instrument should pass when the surgeon makes an incision with the surgical instrument, achieving the safe incision.

The incision initiation determination unit 39 determines whether the position of the tip portion detected by the surgical instrument tip detector 35 has reached the incision line estimated by the incision line estimation unit 38.

The incision initiation notification unit 40 notifies the surgeon of the possibility of starting the incision when the incision initiation determination unit 39 determines that the position has reached the incision line.

Figure 5:
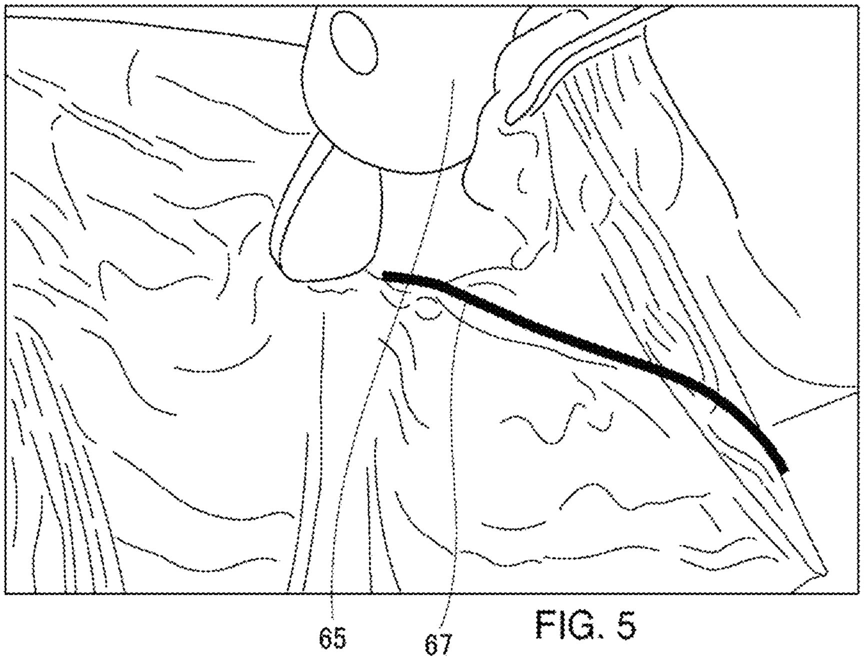
FIG. 5 is a diagram illustrating an example of an incision mark made by actual surgery for the surgery assisting system.
Figure 6:
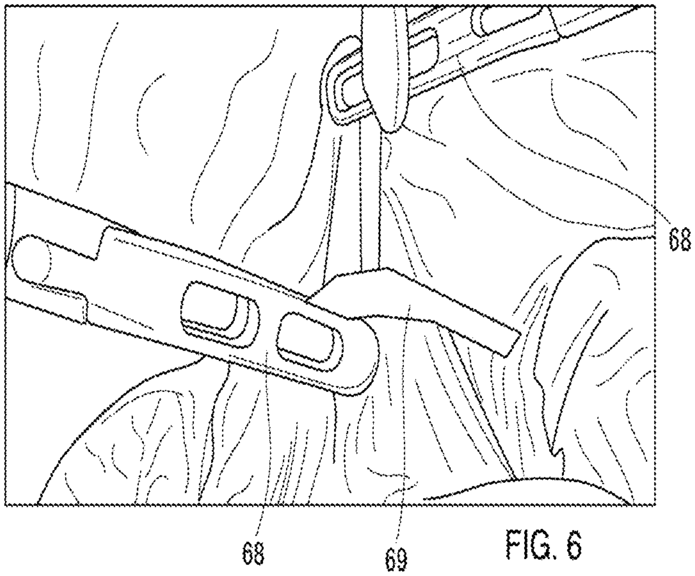
FIG. 6 is a diagram illustrating an example of an image annotated with a pre-incision image of an incision point by an actual surgery for the surgery assisting system.
Figure 7:
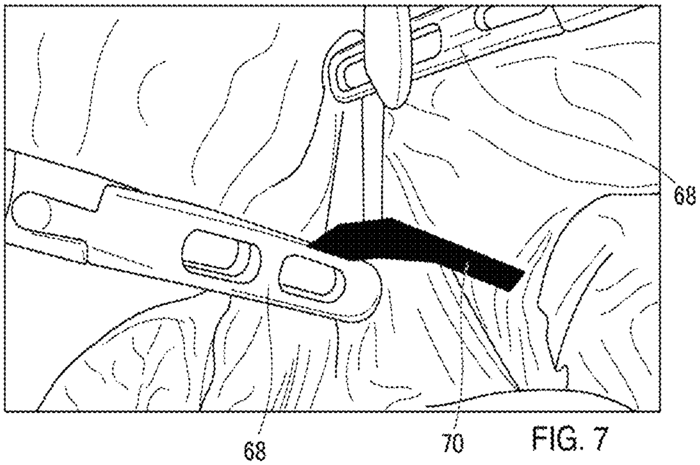
FIG. 7 is a diagram illustrating an example of an image captured by an endoscope for the surgery assisting system, with an incision line highlighted and superimposed on the image captured by the endoscope.

With reference to FIGS. 5 through 7 the learning data for the incision line estimation model will be described. FIG. 5 is a diagram illustrating an example of actual surgical incision mark for the surgery assisting system 10, FIG. 6 is an image annotated with a pre-incision image of an incision point by an actual surgery for the surgery assisting system 10, and FIG. 7 is a diagram illustrating an example of an image captured by the endoscope for the surgery assisting system 10, with an incision line highlighted and superimposed on the image captured by the endoscope.

The image FIG. 5 shows the actual incision line 67 during the surgery with the surgical energy device 65. In the video of the incision during the surgery, the image in FIG. 6 corresponds to the image before the incision of the incision point, rewound for a predetermined time from the image in FIG. 5. The teacher data is generated by annotating positions in the image in FIG. 6, which correspond to the incision points in FIG. 5, with annotation 69.

The incision line estimation model is generated by learning in advance the relationship among the image before incision at the incision point by the surgery (corresponding to the image before annotation 69 in FIG. 6 is assigned), the image obtained by annotating the image before annotation with the trajectory of the tip portion of the surgical instrument at the time of incision as annotation 69 (corresponding to FIG. 6), and the organ for the process of the surgical technique of the surgery.

The organ area estimation unit 33 estimates the position and range of the incision line in the image acquired by the image acquisition unit 31 through which the tip portion of the surgical instrument should pass at the time of incision, and the estimated area display unit 44 superimposes and displays a highlight 70 on the position and range of the incision line estimated by the organ area estimation unit 33 in the image acquired by the image acquisition unit 31 as shown in FIG. 7.

Vascular Injury Determination Mode

The vascular injury determination mode of the surgery assisting system 10 detects when a blood vessel is injured by a surgical instrument during the surgery and notifies it to the surgeon or other person.

The vascular detector 41 detects the position and range of blood vessel(s) in the image acquired by the image acquisition unit 31. The vascular detector 41 detects blood vessel(s) in the image using known image recognition methods. For example, the vascular detector 41 detects blood vessels in an image using a pattern recognition model that has learned in advance the patterns of blood vessel images. The vascular detector 41 inputs the image acquired by the image acquisition unit 31 into the pattern recognition model, and the pattern recognition model detects portions in the image, which are similar to the pattern image of blood vessels.

The vascular injury determination unit 42 determines whether the position of the tip portion detected by the surgical instrument tip detector 35 has reached the blood vessel(s) detected by the vascular detector 41.

The vascular injury notification unit 43 notifies the surgeon of the possibility of the vascular injury when the vascular injury determination unit 42 determines that the position has reached the blood vessel(s). The method of notification by the vascular injury notification unit 43 may include the display of a predetermined notification screen on the monitor 12 and smart glasses 13, and the sounding of a predetermined alarm tone by the smart glasses 13 and speaker 26.

Estimated Area Display Unit

An estimated area display unit 44 displays information indicating the location and range of a certain organ estimated by the organ area estimation unit 33, superimposed on the image acquired by the image acquisition unit 31.

The estimated area display unit 44 performs semantic segmentation on the location and range of the certain organ as estimated by the organ area estimation unit 33. The semantic segmentation is directed to a method of classifying each pixel in an image into a certain category so that every pixel in the image is classified into the certain category.

Figure 8:
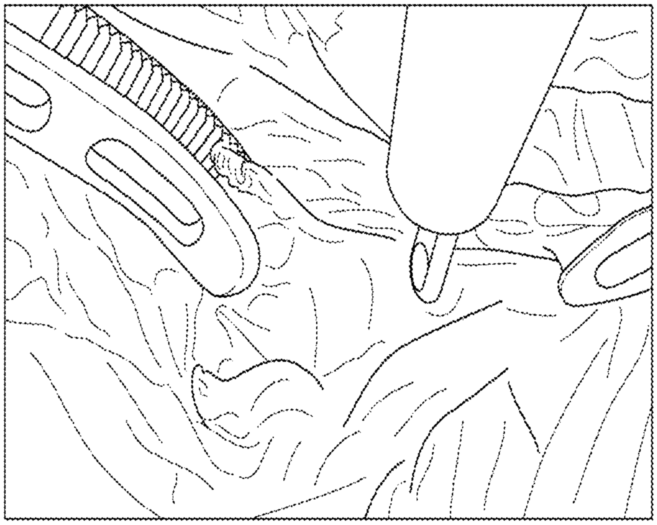
FIG. 8 is a diagram illustrating an example of an image captured by the endoscope for the surgery assisting system.
Figure 9:
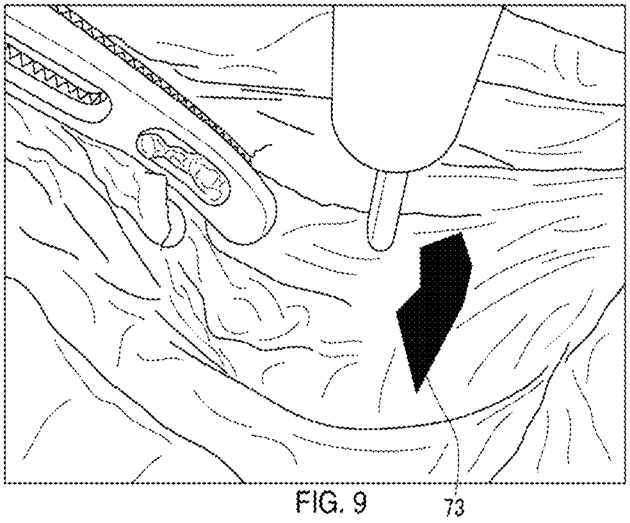
FIG. 9 is a diagram illustrating an example of a display of an image captured by the endoscope on which highlighted position and range of organs that are likely to be damaged during surgery for the surgery assisting system are superimposed.

With reference to FIGS. 8 and 9, the form in which the information indicating the estimation results of the organ area estimation unit 33 in the estimated area display unit 44 is superimposed on the image acquired by the image acquisition unit 31 will be described.

FIG. 8 is a diagram illustrating an example of the image captured by the endoscope for the surgery assisting system 10, and FIG. 9 is a diagram illustrating an example of a display of the image captured by the endoscope on which highlighted position and range of organs with a high probability of being damaged during the surgery for the surgery assisting system 10 are superimposed.

The estimated region display unit 44 superimposes information (highlight 73) indicating the estimation results (see FIG. 9) of the organ area estimation unit 33 on the images (see FIG. 8) acquired by the image acquisition unit 31.

The categories are directed to each organ and each surgical instrument. The estimated area display unit 44 performs semantic segmentation on the images to classify and display each organ and each surgical instrument in an individually identifiable manner. The estimated area display unit 44 uses the same display form for the same organ and the same surgical instrument in the area where they are present. The estimated area display unit 44 changes the display forms such as color, density, brightness, hatching pattern, and blinking pattern for each organ and for each surgical instrument to enable identification of each organ and each surgical instrument.

When the organ area estimation unit 33 estimates the position and range of a plurality of certain organs in the image acquired by the image acquisition unit 31, the estimated area display unit 44 superimposes and displays the information indicating the certain organs estimated by the organ area estimation unit 33 on the image acquired by the image acquisition unit 31 in different display forms, respectively.

The organ area estimation model learns in advance the form of movement related to the automaticity if the organ to be learned has automaticity. If the certain organ estimated by the organ area estimation unit 33 has automaticity, the estimated area display unit 44 highlights the information indicating the certain organ estimated by the organ area estimation unit 33 in a certain manner and superimposes it on the images acquired by the image acquisition unit 31.

Exposure Degree Determination Mode

The exposure degree determination mode of the surgery assisting system 10 changes the display mode of information indicating the certain organ in the estimated area display unit 44 in accordance with the exposure degree of the certain organ estimated by the organ area estimation unit 33.

The exposure degree determination unit 34 determines the degree of exposure of the certain organ by comparing the position and range of the certain organ estimated by the organ area estimation unit 33 with the images acquired by the image acquisition unit 31. The estimated area display unit 44 changes the display form of information indicating the certain organ estimated by the organ area estimation unit 33 in accordance with the exposure degree determined by the exposure degree determination unit 34.

Tracking

The image acquisition unit 31 may acquire a plurality of consecutive images, and the organ area estimation unit 33 may estimate the trajectory of the position and range of the certain organ(s) by inputting the consecutive images acquired by the image acquisition unit 31 into the organ area estimation model.

For example, the image acquisition unit 31 acquires 10 images captured at certain intervals (e.g., one second) by the endoscope, and the organ area estimation unit 33 inputs the 10 images into the organ area estimation model to estimate the position and range of the certain organ for each image. The estimated area display unit 44 superimposes the information indicating the 10 positions and ranges of a certain organ estimated by the organ area estimation unit 33 on the image acquired by the image acquisition unit 31, thereby showing the trajectory of the certain organ for 10 seconds to the surgeon.

CT and MRI

The image acquisition unit 31 acquires at least one of the image captured by the computed tomography (CT) before the surgery and image captured by the magnetic resonance imaging (MRI) before the surgery along with the image captured by the endoscope, the organ area estimation unit 33 estimates the position and range of a certain organ(s) by inputting the image acquired by the image acquisition unit 31 into an organ area estimation model, and the estimated area display unit 44 superimposes and displays the information indicating the position and range of the certain organ(s) estimated by the organ area estimation unit 33 on at least one of the image captured by the computed tomography (CT) before the surgery and the image captured by the magnetic resonance imaging (MRI) before the surgery, which are acquired by the image acquisition unit 31.

The computed tomography (CT) and magnetic resonance imaging (MRI) are capable of displaying the inside of the human body by means of three-dimensional images. The estimation area display unit 44 superimposes the information indicating the position and range of the certain organ estimated by the organ area estimation unit 33 on a three-dimensional image captured by at least one of the computed tomography (CT) and magnetic resonance imaging (MRI) to show the certain organ to the surgeon in an easily understandable manner.

Figure 10:
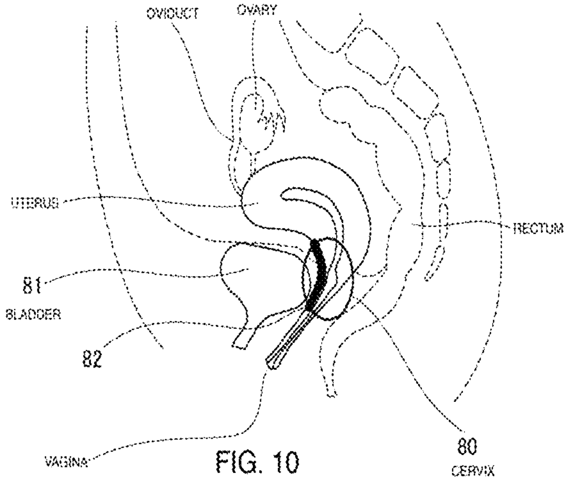
FIG. 10 is a diagram illustrating an example of an image captured by the endoscope on which highlighted position and range of the cervix on the side of the cervix closer to the bladder for the surgery assisting system are superimposed.

With reference to FIG. 10, a form will be described in which the position and range of the cervix 80 on the side closer to the bladder 81 are highlighted and superimposed on the image captured by the endoscope. FIG. 10 is a diagram illustrating an example of the image captured by the endoscope on which the position and range of the cervix 80 on the side of the cervix 80 closer to the bladder 81 are highlighted and superimposed (82) for the surgery assisting system 10.

When the endoscope corresponds to a laparoscope and the organ area estimation unit 33 estimates the position and range of two adjacent organs by inputting the image acquired by the image acquisition unit 31 into the organ area estimation model, the estimation area display unit 44 superimposes and displays, from among the information indicating the position and range of one of the two adjacent organs, the portion closer to the position and range of the other of the two adjacent organs on the image acquired by the image acquisition unit 31.

The two adjacent organs correspond to two organs that are so close to each other that a risk may be caused in which a surgical instrument, for example, may be brought into contact with the other organ during the treatment of one organ.

For example, as shown in FIG. 10, if the organ area estimation unit 33 estimates the position and range of the bladder 81 and the cervix 80, the estimated region display unit 44 superimposes and displays, from among the information indicating the position and range of the cervix 80, the portion 82 which is close to the position and range of the bladder 81, on the image acquired by the image acquisition unit 31.

When a surgeon is administering a treatment on one of two adjacent organs, a portion near the other organ is likely to be damaged by the surgeon. In such instances, highlighting the portion of one organ that is close to the other organ can alert the surgeon to the portion of one organ that is most likely to be damaged, thereby effectively reducing the occurrence of intraoperative accidents for the surgeon.

In the example in FIG. 10, the portion of the cervix 80 near the bladder 81 is likely to be damaged by the surgeon. Accordingly, the portion of the cervix 80 near the bladder 81 is highlighted.

Surgery Assisting Method and Surgery Assisting Program

Next, with reference to FIGS. 11 through 14, the surgery assisting method will be described along with the surgery assisting program. FIGS. 11 through 14 are flowcharts of the surgery assisting program.

The surgery assisting system 10 operates in four modes (exposure degree determination mode, organ damage determination mode, incision initiation determination mode, and vascular damage determination mode) by executing the surgery assisting program. The surgery assisting method and surgery assisting program shall be described by describing the respective flowcharts for the exposure degree determination mode, organ damage determination mode, incision initiation determination mode, and vascular damage determination mode.

Figure 11:
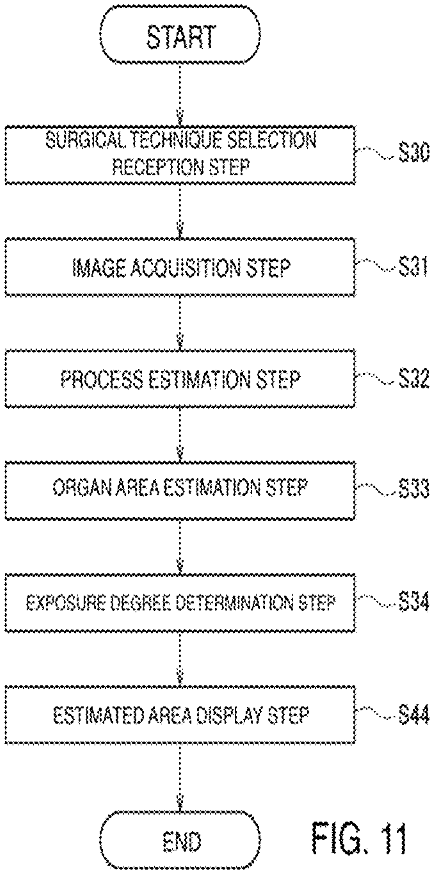
FIG. 11 is a flowchart illustrating an organ exposure degree determination mode for a surgery assisting program.
Figure 12:
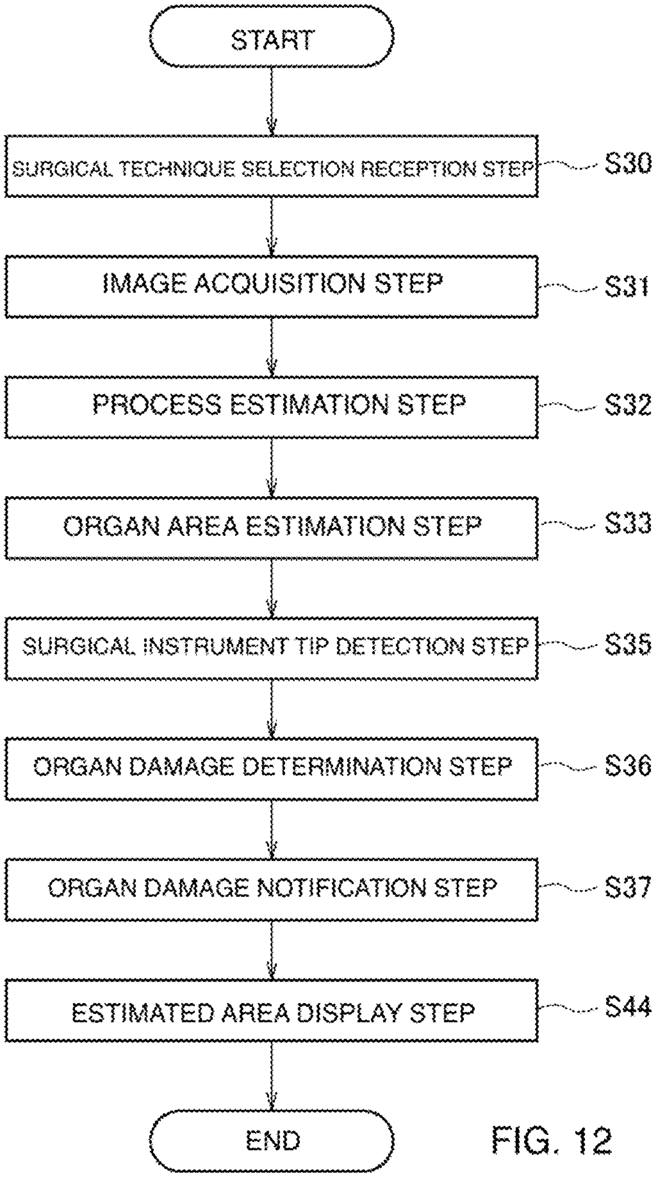
FIG. 12 is a flowchart illustrating an organ damage determination mode for the surgery assisting program.
Figure 13:
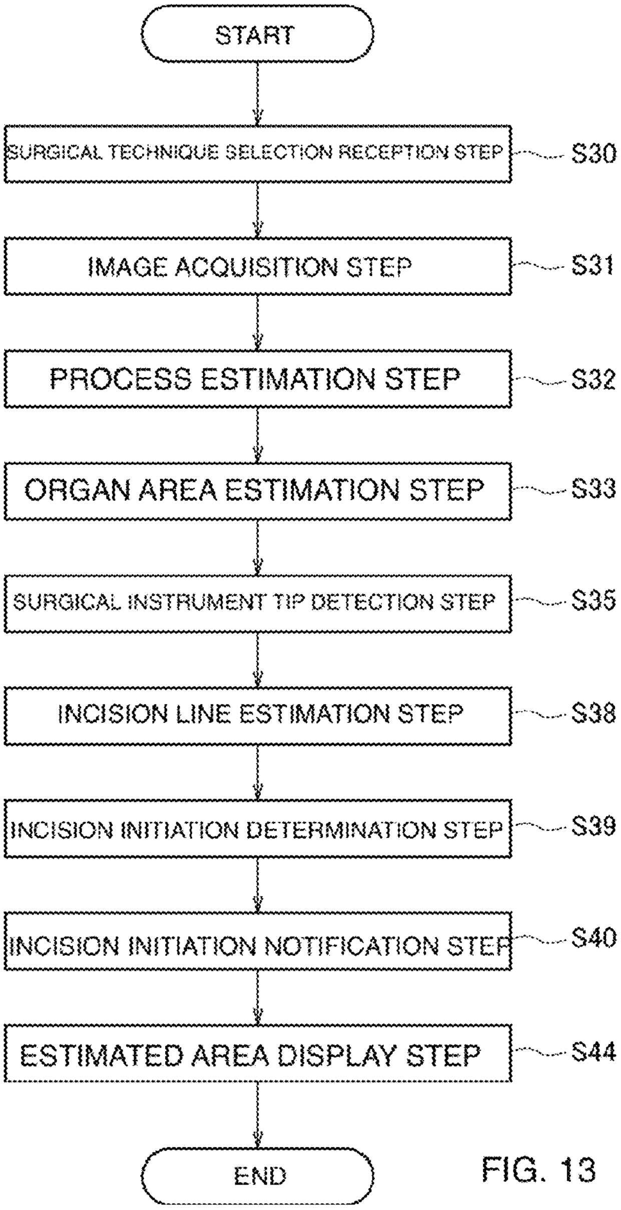
FIG. 13 is a flowchart illustrating an incision initiation determination mode for the surgery assisting program.
Figure 14:
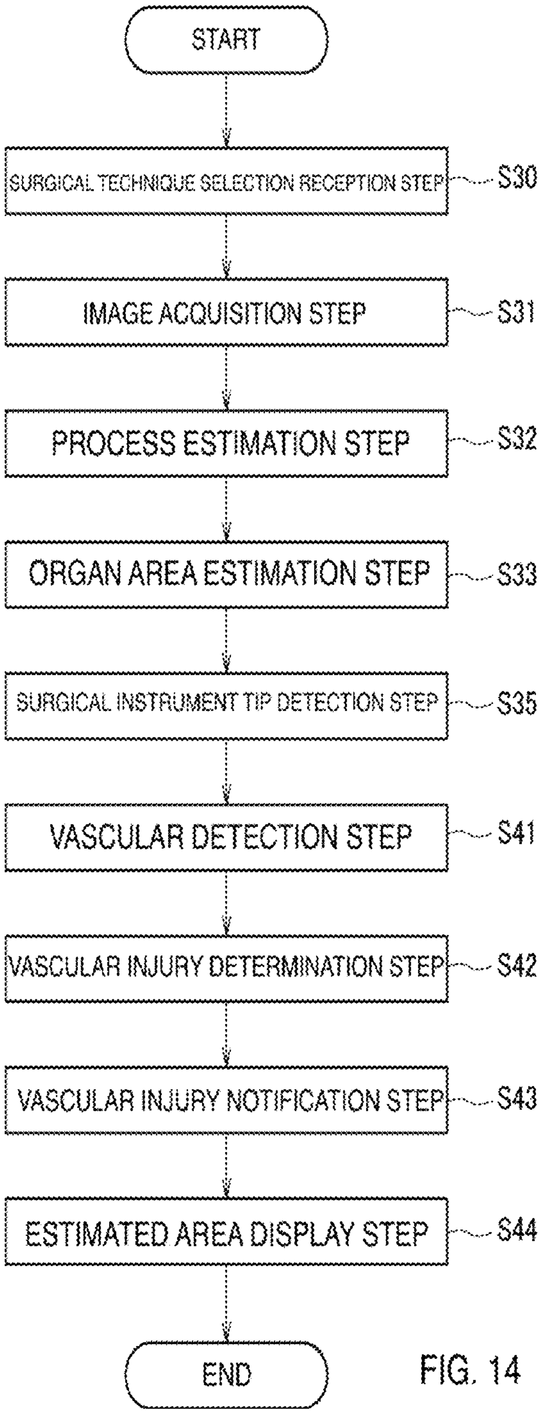
FIG. 14 is a flowchart illustrating an vascular injury determination mode for the surgery assisting program.

FIG. 11 is a flowchart of an organ exposure degree determination mode for a surgery assisting program, FIG. 12 is a flowchart of an organ damage determination mode for the surgery assisting program, FIG. 13 is a flowchart of an incision initiation determination mode for the surgery assisting program, and FIG. 14 is a flowchart of a vascular injury determination mode for the surgery assisting program.

Organ Exposure Degree Determination Mode

As shown in FIG. 11, the flowchart of the organ exposure degree determination mode may include: the surgical technique selection reception step S30, image acquisition step S31, process estimation step S32, organ area estimation step S33, exposure degree determination step S34, and estimated area display step S44.

The surgery assisting system 10 reads the surgery assisting program stored in the ROM 10*b* or storage 10*d* into the main memory and executes the surgery assisting program associated with the organ exposure degree determination mode by the CPU 10*e*.

The surgery assisting program associated with the organ exposure determination mode causes the CPU 10*e* of the surgery assisting system 10 to embody various functions such as the surgical technique selection reception function, image acquisition function, process estimation function, organ area estimation function, exposure degree determination function, and estimated area display function.

Although these functions are illustrated to be performed in the order shown in the flowchart in FIG. 11, they are not limited to this order, and the surgery assisting program associated with the organ exposure determination mode may be executed by changing the order of these functions as appropriate.

Since the description of the functions described above is redundant with the description of the surgical technique selection reception unit 30, image acquisition unit 31, process estimation unit 32, organ area estimation unit 33, exposure degree determination unit 34, and estimated area display unit 44, a detailed description thereof is omitted.

The surgical technique selection reception function accepts the selection of a surgical technique of the surgery (step S30: surgical technique selection reception step).

The image acquisition function acquires images captured by the endoscope (step S31: image acquisition step).

The process estimation function estimates the process of the surgical technique in the images acquired by the image acquisition function by inputting the images acquired by the image acquisition function and the identification information indicating the surgical technique accepted by the surgical technique selection reception function into a process classification model that has classified a series of processes of the surgical technique of the surgery from start to end for each content and learned the relationship between each process in the series of processes sequentially performed and the images captured during the surgery in advance (step S32: process estimation step).

The organ area estimation function inputs the images acquired by the image acquisition function into the organ area estimation model, which has learned in advance the relationship between the images captured during the surgery and the position and range of a certain organ(s) in the image, and estimates the position and range of the certain organ(s) in the images acquired by the image acquisition function (step S33: organ area estimation step).

The exposure degree determination function determines the exposure degree of the certain organ(s) by comparing the position and range of the certain organ(s) estimated by the organ area estimation function with the images acquired by the image acquisition function (step S34: exposure degree determination step).

The estimated area display function superimposes the information indicating the position and range of the certain organ estimated by the organ area estimation function on the image acquired by the image acquisition function (step S44: estimated area display step).

Organ Damage Determination Mode

As shown in FIG. 12, the flowchart of the organ damage determination mode may include the following steps: surgical technique selection reception step S30, image acquisition step S31, process estimation step S32, organ area estimation step S33, surgical instrument tip detection step S35, organ damage determination step S36, organ damage notification step S37, and estimated area display step S44, for example.

The surgery assisting system 10 reads the surgery assisting program stored in the ROM 10*b* or storage 10*d* into the main memory and executes the surgery assisting program associated with the organ damage determination mode by the CPU 10*c*.

The surgery assisting program associated with the organ damage determination mode causes the CPU 10*e* of the surgery assisting system 10 to embody various functions such as the surgical technique selection reception function, image acquisition function, process estimation function, organ area estimation function, surgical instrument tip detection function, organ damage determination function, organ damage notification function, and estimated area display function.

Although these functions are illustrated to be performed in the order shown in the flowchart in FIG. 12, they are not limited to this order, and the surgery assisting program associated with the organ damage determination mode may be executed by changing the order of these functions as appropriate.

Since the description of the functions above is redundant with the description of the surgical technique selection reception unit 30, image acquisition unit 31, process estimation unit 32, organ area estimation unit 33, surgical instrument tip detector 35, organ damage determination unit 36, organ damage notification unit 37, and estimated area display unit 44, the detailed description thereof is omitted.

The surgical technique selection reception function accepts the selection of a surgical technique of the surgery (step S30: surgical technique selection reception step).

The image acquisition function acquires images captured by the endoscope (step S31: image acquisition step).

The process estimation function estimates the process of the surgical technique in the images acquired by the image acquisition function by inputting the images acquired by the image acquisition function and the identification information indicating the surgical technique accepted by the surgical technique selection reception function into a process classification model that has classified a series of processes of the surgical technique of the surgery from start to end for each content and learned the relationship between each process in the series of processes sequentially performed and the images captured during the surgery in advance (step S32: process estimation step).

The organ area estimation function inputs the images acquired by the image acquisition function into the organ area estimation model, which has learned in advance the relationship between the images captured during the surgery and the position and range of a certain organ(s) in the image, and estimates the position and range of the certain organ(s) in the images acquired by the image acquisition function (step S33: organ area estimation step).

The surgical instrument tip detection function detects the position of the tip portion of the surgical instrument in the images acquired by the image acquisition function using a surgical instrument detection model that has learned in advance the shape of the tip portion of the surgical instrument (step S35: surgical instrument tip detection step).

The organ damage determination function determines whether the position of the tip portion detected by the surgical instrument tip detection function has reached the position and range of the certain organ estimated by the organ area estimation function (step S36: organ damage determination step).

The organ damage notification function notifies the surgeon of the possibility of organ damage when the organ damage determination function determines that the position of the tip portion has reached the estimated position and range (step S37: organ damage notification step).

The estimated area display function superimposes the information indicating the position and range of the certain organ estimated by the organ area estimation function on the image acquired by the image acquisition function (step S44: estimated area display step).

Incision Initiation Determination Mode

As shown in FIG. 13, the flowchart of the incision initiation determination mode may include the following steps: surgical technique selection reception step S30, image acquisition step S31, process estimation step S32, organ area estimation step S33, surgical instrument tip detection step S35, incision line estimation step S38, incision initiation determination step S39, incision initiation notification step S40, and estimated area display step S44, for example.

The surgery assisting system 10 reads the surgery assisting program stored in the ROM 10*b* or storage 10*d* into the main memory and executes the surgery assisting program associated with the incision initiation determination mode by the CPU 10*c*.

The surgery assisting program associated with the incision initiation determination mode causes the CPU 10*e* of the surgery assisting system 10 to embody various functions such as the surgical technique selection reception function, image acquisition function, process estimation function, organ area estimation function, surgical instrument tip detection function, incision line estimation function, incision initiation determination function, incision initiation notification function, and estimated area display function.

Although these functions are illustrated to be performed in the order shown in the flowchart in FIG. 14, they are not limited to this order, and the surgery assisting program associated with the vascular injury determination mode may be executed by changing the order of these functions as appropriate.

Since the description of the functions above is redundant with the description of the surgical technique selection reception unit 30, image acquisition unit 31, process estimation unit 32, organ area estimation unit 33, surgical instrument tip detector 35, incision line estimation unit 38, incision initiation determination unit 39, incision initiation notification unit 40, and estimated area display unit 44, the detailed description thereof is omitted.

The surgical technique selection reception function accepts the selection of a surgical technique of the operation (step S30: surgical technique selection reception step).

The image acquisition function acquires images captured by the endoscope (step S31: image acquisition step).

The process estimation function estimates the process of the surgical technique in the images acquired by the image acquisition function by inputting the images acquired by the image acquisition function and the identification information indicating the surgical technique accepted by the surgical technique selection reception function into a process classification model that has classified a series of processes of the surgical technique of the surgery from start to end for each content and learned the relationship between each process in the series of processes sequentially performed and the images captured during the surgery in advance (step S32: process estimation step).

The organ area estimation function inputs the images acquired by the image acquisition function into the organ area estimation model, which has learned in advance the relationship between the images captured during the surgery and the position and range of a certain organ(s) in the image, and estimates the position and range of the certain organ(s) in the images acquired by the image acquisition function (step S33: organ area estimation step).

The surgical instrument tip detection function detects the position of the tip portion of the surgical instrument in the images acquired by the image acquisition function using a surgical instrument detection model that has learned in advance the shape of the tip portion of the surgical instrument (step S35: surgical instrument tip detection step).

The incision line estimation function inputs the images acquired by the image acquisition function, the identification information indicating the surgical technique accepted by the surgical technique selection reception function, and the identification information indicating the process estimated by the process estimation function into the incision line estimation model that has learned in advance the relationship among the organ(s) for the process of the surgical technique of the surgery, the images before the incision at the incision point by the surgery, and the images acquired by annotating the images before the incision with the trajectory of the tip portion of the surgical instrument at the time of the incision to estimate the position and range of the incision line through which the tip portion of the surgical instrument should pass at the time of incision in the images acquired by the image acquisition function (step S38: incision line estimation step).

The incision initiation determination function determines whether the position of the tip portion detected by the surgical instrument tip detection function has reached the incision line estimated by the incision line estimation function (step S39: incision initiation determination step).

The incision initiation notification function notifies the surgeon of the possibility of initiating an incision when the incision initiation determination function determines that the position of the tip portion has reached the incision line (step S40: incision initiation notification step).

Vascular Injury Determination Mode

As shown in FIG. 14, the flowchart of the vascular injury determination mode may include the following steps: surgical technique selection reception step S30, image acquisition step S31, process estimation step S32, organ area estimation step S33, surgical instrument tip detection step S35, vascular detection step S41, vascular injury determination step S42, vascular injury notification step S43, and estimated area display step S44, for example.

The surgery assisting system 10 reads the surgery assisting program stored in the ROM 10*b* or storage 10*d* into the main memory and executes the surgery assisting program associated with the vascular injury determination mode by the CPU 10*c*.

The surgery assisting program associated with the vascular injury determination mode causes the CPU 10*e* of the surgery assisting system 10 to embody various functions such as the surgical technique selection reception function, image acquisition function, process estimation function, organ area estimation function, surgical instrument tip detection function, vascular detection function, vascular injury determination function, vascular injury notification function, and estimated area display function.

Although these functions are illustrated to be performed in the order shown in the flowchart in FIG. 14, they are not limited to this order, and the surgery assisting program associated with the vascular injury determination mode may be executed by changing the order of these functions as appropriate.

Since the description of the functions above is redundant with the description of the surgical technique selection reception unit 30, image acquisition unit 31, process estimation unit 32, organ area estimation unit 33, surgical instrument tip detector 35, vascular detector 41, vascular injury determination unit 42, vascular injury notification unit 43, and estimated area display unit 44, the detailed description thereof is omitted.

The surgical technique selection reception function accepts the selection of a surgical technique of the operation (step S30: surgical technique selection reception step).

The image acquisition function acquires images captured by the endoscope (step S31: image acquisition step).

The process estimation function estimates the process of the surgical technique in the images acquired by the image acquisition function by inputting the images acquired by the image acquisition function and the identification information indicating the surgical technique accepted by the surgical technique selection reception function into a process classification model that has classified a series of processes of the surgical technique of the surgery from start to end for each content and learned the relationship between each process in the series of processes sequentially performed and the images captured during the surgery in advance (step S32: process estimation step).

The organ area estimation function inputs the images acquired by the image acquisition function into the organ area estimation model, which has learned in advance the relationship between the images captured during the surgery and the position and range of a certain organ(s) in the image, and estimates the position and range of the certain organ(s) in the images acquired by the image acquisition function (step S33: organ area estimation step).

The surgical instrument tip detection function detects the position of the tip portion of the surgical instrument in the images acquired by the image acquisition function using a surgical instrument detection model that has learned in advance the shape of the tip portion of the surgical instrument (step S35: surgical instrument tip detection step).

The vascular detection function detects the position and range of blood vessels in the image acquired by the image acquisition function (step S41: vascular detection step).

The vascular injury determination function determines whether the position of the tip portion detected by the surgical instrument tip detection function has reached the blood vessel detected by the vascular detection function (step S42: vascular injury determination step).

The vascular injury notification function notifies the surgeon of the possibility of vascular injury when the vascular injury determination function determines that the position of the tip portion has reached the detected blood vessel(s) (step S43: vascular injury notification step).

The estimated area display function superimposes the information indicating the position and range of the certain organ estimated by the organ area estimation function on the image acquired by the image acquisition function (step S44: estimated area display step).

Generation Process of Learning Model

Figure 15:
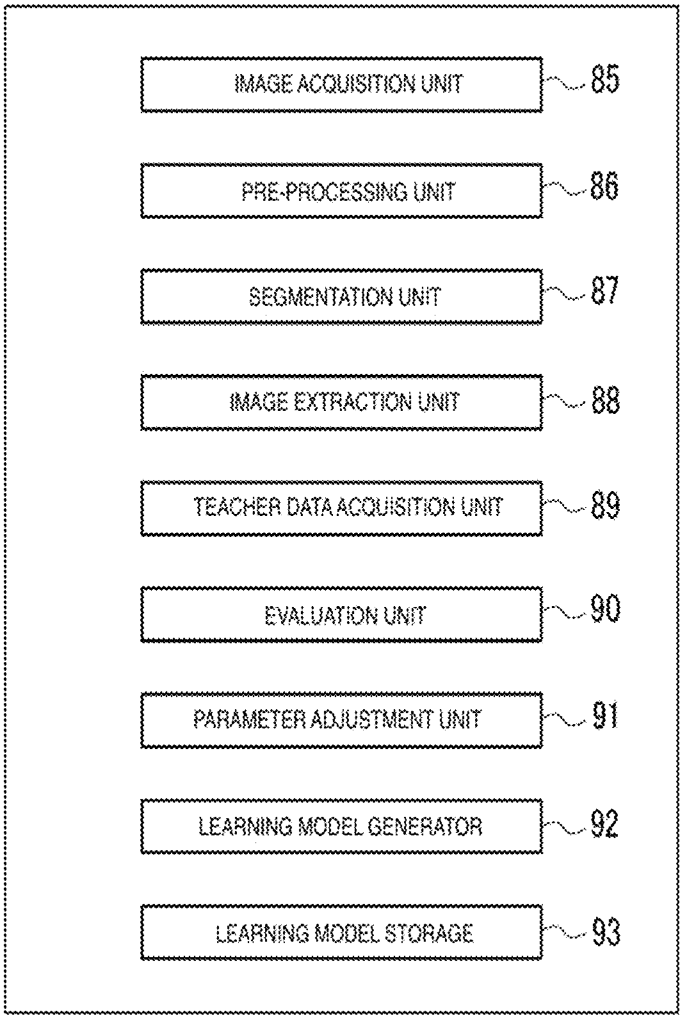
FIG. 15 is a functional block diagram in a process of generating a learning model for the surgery assisting system.
Figure 16:
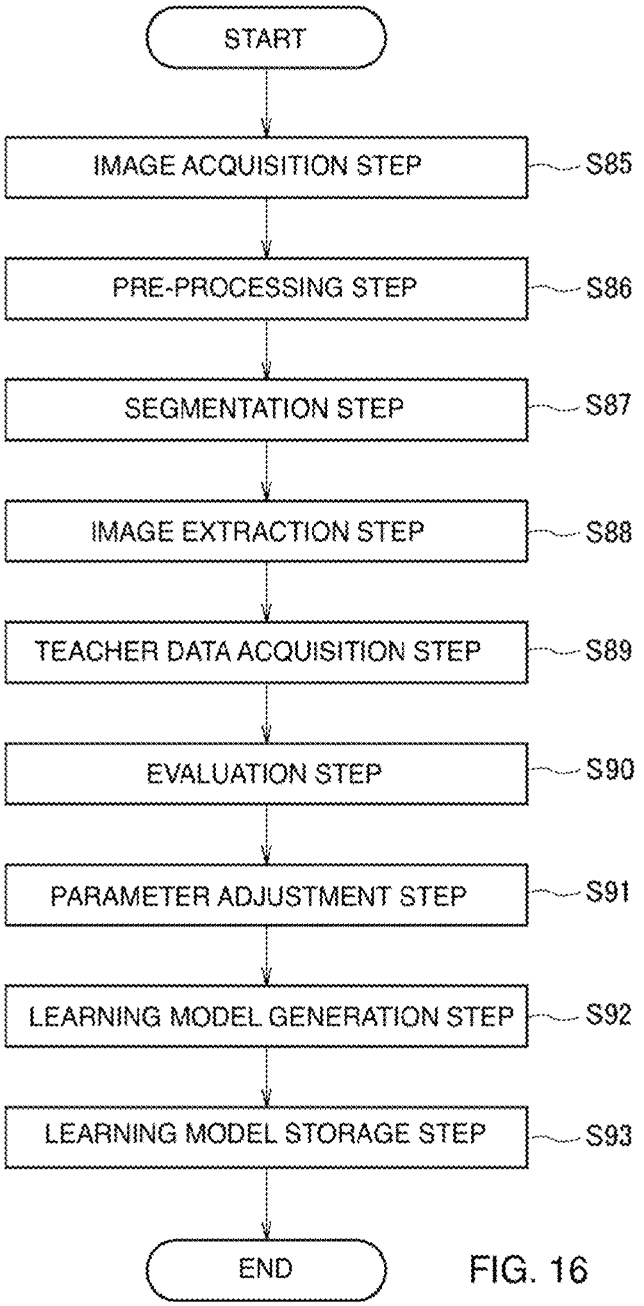
FIG. 16 is a flowchart illustrating the process of generating a learning model for the surgery assisting system.

With reference to FIGS. 15 and 16, the process of generating the learning models (organ area estimation model, process classification model, and incision line estimation model) of the surgery assisting system 10 will be described next. FIG. 15 is a functional block diagram in a process of generating a learning model for the surgery assisting system 10, and FIG. 16 is a flowchart of a program of generating a learning model for the surgery assisting system 10 (hereinafter, referred to as a learning model generation program).

First, with reference to FIG. 15, the functional configuration in the process of generating the learning model of the surgery assisting system 10 will be described.

The surgery assisting system 10 stores the learning model generation program needed in the process of generating the learning model in the ROM 10*b* or storage 10*d*, and reads the learning model generation program in the main memory configured by the RAM 10*c*, for example. The CPU 10*e* executes the learning model generation program by accessing the main memory that contains the learning model generation program.

The surgery assisting system 10 executes the learning model generation program to provide the CPU 10*e* with functional units such as the image acquisition unit 85, pre-processing unit 86, segmentation unit 87, image extraction unit 88, teacher data acquisition unit 89, evaluation unit 90, parameter adjustment unit 91, learning model generator 92, and learning model storage 93.

The image acquisition unit 85 acquires the images captured during the surgery, which are stored in the RAM 10*c* or storage 10*d*.

The image acquisition unit 85 may acquire the images captured during the surgery, which are stored outside of the surgery assisting system 10 from the network 11 via the communication interface 10*a*.

The pre-processing unit 86 performs pre-processing on the image acquired by the image acquisition unit 85.

The pre-processing refers to the processing that is performed on the regularities (features) of the image to be input into the learning model before inputting the image into the learning model to allow the learning model to learn. The pre-processing may include highlighting features, removing noise, and increasing features. The processes to highlight features may include grayscale conversion, binarization, and normalization. The processes to remove noise may include morphological conversion, histogram, dimensional compression, and resizing. The processes to increase features may include image padding such as inversion, smoothing, and brightness change of the image.

The segmentation unit 87 performs segmentation on the image that has been pre-processed by the pre-processing unit 86, dividing it into regions for each object present in the image.

The segmentation unit 87 performs segmentation using a neural network.

The image extraction unit 88 extracts the image of the object on which image recognition is to be performed from the images for which segmentation has been performed by the segmentation unit 87.

An object in learning an organ area estimation model is directed to a certain organ or region. The certain organ(s) or region may include, for example, an organ or region that is likely to be damaged during the surgery.

An object in learning a process classification model is directed to an organ(s) in the image.

An object in learning the incision line estimation model is directed to an organ(s) and incision line in the image.

The teacher data acquisition unit 89 acquires the teacher data stored in the RAM 10*c* or storage 10*d*.

The teacher data acquisition unit 89 may acquire the teacher data stored outside the surgery assisting system 10 from the network 11 via the communication interface 10*a*.

The teacher data is acquired by annotating the object in the images captured during the surgery by assigning contour line information (segmentation) to the area occupied by the object on which the image recognition is to be performed, followed by labeling to assign features such as the name of the organ or region of the body in that area.

The teacher data for the organ area estimation model corresponds to images in which the position and range of the organ(s) on which image recognition is to be performed is annotated.

The teacher data for the process classification model corresponds to an image annotated with the name of the process on which the image recognition is to be performed.

The teacher data for the incision line estimation model corresponds to images in which the position and range of the incision line on which image recognition is to be performed are annotated.

The evaluation unit 90 evaluates the learning model by computing the error between the image extracted by the image extraction unit 88 and the teacher data acquired by the teacher data acquisition unit 89 using the error function.

The error function is directed to a function that represents the magnitude of the discrepancy between the image extracted by the image extraction unit 88 and the teacher data acquired by the teacher data acquisition unit 89, and evaluates the prediction accuracy of the learning model. The less the value of the error function is, the more accurate the learning model is evaluated to be.

The parameter adjustment unit 91 adjusts the parameters representing the weight coefficients of the neural network used in the learning model to minimize the value of the error function computed by the evaluation unit 90.

The parameter adjustment unit 91 uses the error back propagation method to propagate the value of the error function to each layer of the neural network used in the learning model to adjust the parameters representing the weight coefficients of each layer to minimize the error.

The learning model generator 92 generates the learning model using the parameters adjusted by the parameter adjustment unit 91 to minimize the value of the error function.

The learning model storage unit 93 stores the learning model generated by the learning model generator 92 in the RAM 10*c* or storage 10*d*.

Although the surgery assisting system 10 generates the learning model, the model is not limited to this, and an electronic computer different from the surgery assisting system 10 may generate the learning model for the surgery assisting system 10.

With reference to FIG. 16, the learning model generation program of the surgery assisting system 10 will be described next.

As shown in FIG. 16, the learning model generation program may include: the image acquisition step S85, pre-processing step S86, segmentation step S87, image extraction step S88, teacher data acquisition step S89, evaluation step S90, parameter adjustment step S91, learning model generation step S92, and learning model storage step S93, for example.

The surgery assisting system 10 reads the learning model generation program stored in the ROM 10*b* or storage 10*d* into the main memory and executes the learning model generation program by the CPU 10*e*.

The learning model generation program causes the CPU 10*e* of the surgery assisting system 10 to embody various functions such as the image acquisition function, pre-processing function, segmentation function, image extraction function, teacher data acquisition function, evaluation function, parameter adjustment function, learning model generation function, and learning model storage function, for example.

Although these functions are illustrated to be performed in the order shown in the flowchart in FIG. 16, they are not limited to this order, and the learning model generation program may be executed by changing the order of these functions as appropriate.

Since the description of the functions above is redundant with the description of the image acquisition unit 85, pre-processing unit 86, segmentation unit 87, image extraction unit 88, teacher data acquisition unit 89, evaluation unit 90, parameter adjustment unit 91, learning model generator 92, and learning model storage 93, the detailed description thereof is omitted.

The image acquisition function acquires images captured during the surgery, which are stored in the RAM 10*c* or storage 10*d* (step S85: image acquisition step).

The pre-processing function performs pre-processing on the image acquired by the image acquisition function (step S86: pre-processing step).

The segmentation function performs segmentation on each image that has been pre-processed by the pre-processing function into areas for each object present in the image (step S87: segmentation step).

The image extraction function extracts each image of the object on which the image recognition is to be performed from the image on which the segmentation has been performed by the segmentation function (step S88: image extraction step).

The teacher data acquisition function acquires the teacher data stored in the RAM 10*c* or storage 10*d* (step S89: teacher data acquisition step).

The evaluation function evaluates the learning model by computing the error between the image extracted by the image extraction function and the teacher data acquired by the teacher data acquisition function using the error function (step S90: evaluation step).

The parameter adjustment function adjusts the parameters representing the weight coefficients of the neural network used in the learning model to minimize the value of the error function computed by the evaluation function (step S91: parameter adjustment step).

The learning model generation function generates a learning model using the parameters adjusted by the parameter adjustment function to minimize the value of the error function (step S92: learning model generation step).

The learning model storage function stores the learning model generated by the learning model generation function in the RAM 10*c* or storage 10*d* (step S93: learning model storage step).

The surgery assisting system 10 inputs the image captured by the endoscope of the endoscope system 14 into the organ area estimation model, allowing the surgery assisting system 10 to immediately estimate the position and range of the organs with a high probability of being damaged during the surgery in the image, thereby superimposing and displaying the organs with a high probability of being damaged during the surgery to the surgeon. This allows the surgeon to perform incisions and other procedures while paying attention to the organs with a high probability of being damaged during the surgery without placing additional device such as cameras in the body cavity of the subject for the purpose of securing a wide field of view during the surgery.

The surgery assisting system 10 can immediately estimate the process of the surgical technique from the image captured by the endoscope of the endoscope system 14 so that the surgery assisting system 10 can show the current process to the surgeon, allowing the surgeon to proceed with the surgery while checking the process of the surgical technique she or he is performing.

The surgery assisting system 10 is capable of indicating to the surgeon the incision line that the tip portion of the surgical instrument should pass through when an incision is performed during surgery, allowing the surgeon to perform the incision with confidence and reducing the possibility of surgical failure.

The present disclosure is not limited to the surgery assisting system 10, surgery assisting method, and surgery assisting program, but may be implemented by various other variations or applications if they do not depart from the spirit of the present disclosure described in the claims.

What is claimed is:

1. A surgery assisting system comprising:

an image acquisition system configured to acquire an image captured by an endoscope;

a surgical technique selection reception system configured to accept a selection of a surgical technique of a surgery;

an organ area estimation system configured to input the image acquired by the image acquisition system and identification information indicating the surgical technique accepted by the surgical technique selection reception system into an organ area estimation model that has learned in advance a relationship among identification information indicating the surgical technique of the surgery, the image captured by the endoscope during the surgery, and a position and range of an organ that is likely to be damaged during the surgery associated with the surgical technique in the image to estimate the position and range of the organ that is likely to be damaged during the surgery in the image acquired by the image acquisition system;

an estimated area display system configured to superimpose and display information indicating the position and range of the organ that is likely to be damaged during the surgery estimated by the organ area estimation system on the image acquired by the image acquisition system;

a surgical instrument tip detector configured to detect a position of a tip portion of a surgical instrument in the image acquired by the image acquisition system using a surgical instrument detection model that has learned in advance a shape of the tip portion of the surgical instrument;

an organ damage determination system configured to determine whether the position of the tip portion detected by the surgical instrument tip detector has reached the organ with a high probability of being damaged during the surgery estimated by the organ area estimation system; and an organ damage notification system configured to notify a surgeon of a possibility of organ damage when the organ damage determination system determines that the position of the tip portion has reached the estimated organ.

2. The surgery assisting system according to claim 1, further comprising:

a surgical instrument tip detector that detects a position of a tip portion of a surgical instrument in the image acquired by the image acquisition system using a surgical instrument detection model that has learned in advance a shape of the tip portion of the surgical instrument;

a vascular detector that detects a position and range of a blood vessel in the image acquired by the image acquisition system;

a vascular injury determination system configured to determine whether the position of the tip portion detected by the surgical instrument tip detector has reached the blood vessel detected by the vascular detector; and a vascular injury notification system configured to notify a surgeon of a possibility of vascular injury when the vascular injury determination system determines that the position of the tip portion has reached the detected blood vessel.

3. The surgery assisting system according to claim 1, wherein the organ area estimation model learns in advance a form of movement associated with automaticity if an organ to be learned has automaticity, and if the organ with a high probability of being damaged during the surgery estimated by the organ area estimation system has automaticity, the estimated area display system superimposes and displays information indicating the organ with a high probability of being damaged during the surgery estimated by the organ area estimation system on the image acquired by the image acquisition system with the information highlighted in a predetermined form.

4. The surgery assisting system according to claim 1, further comprising:

an exposure degree determination system configured to determine an exposure degree of an organ with a high probability of being damaged during the surgery by comparing the position and range of the organ with a high probability of being damaged during the surgery estimated by the organ area estimation system with the image acquired by the image acquisition system, wherein the estimation area display system changes a display form of information indicating the organ that is likely to be damaged during the surgery estimated by the organ area estimation system in accordance with the exposure degree determined by the exposure degree determination system.

5. A surgery assisting method that causes a computer used in a surgery assisting system to perform:

an image acquisition step of acquiring an image captured by an endoscope;

a surgical technique selection reception step of accepting a selection of a surgical technique of a surgery;

an organ area estimation step of inputting the image acquired in the image acquisition step and identification information indicating the surgical technique accepted in the surgical technique selection reception step into an organ area estimation model that has learned in advance a relationship among identification information indicating the surgical technique of the surgery, the image captured by the endoscope during the surgery, and a position and range of an organ that is likely to be damaged during the surgery associated with the surgical technique in the image to estimate the position and range of the organ that is likely to be damaged during the surgery in the image acquired in the image acquisition step;

an estimated area display step of superimposing and displaying information indicating the position and range of the organ that is likely to be damaged during the surgery estimated in the organ area estimation step on the image acquired in the image acquisition step;

a surgical instrument tip detection step of detecting a position of a tip portion of a surgical instrument in the image acquired in the image acquisition step using a surgical instrument detection model that has learned in advance a shape of the tip portion of the surgical instrument;

an organ damage determination step of determining whether the position of the tip portion detected in the surgical instrument tip detection step has reached the organ that is likely to be damaged during the surgery estimated in the organ area estimation step; and an organ damage notification step of notifying a surgeon of a possibility of organ damage when it is determined in the organ damage determination step that the position of the tip portion has reached the estimated organ.

6. A non-transitory computer readable medium storing therein a surgery assisting program that causes a computer used in a surgery assisting system to embody:

an image acquisition function that acquires an image captured by an endoscope;

a surgical technique selection reception function that accepts a selection of a surgical technique of a surgery;

an organ area estimation function that inputs the image acquired by the image acquisition function and identification information indicating the surgical technique accepted by the surgical technique selection reception function into an organ area estimation model that has learned in advance a relationship among identification information indicating the surgical technique of the surgery, the image captured by the endoscope during the surgery, and a position and range of an organ that is likely to be damaged during the surgery associated with the surgical technique in the image to estimate the position and range of the organ that is likely to be damaged during the surgery in the image acquired by the image acquisition function;

an estimated area display function that superimposes and displays information indicating the position and range of the organ that is likely to be damaged during the surgery estimated by the organ area estimation function on the image acquired by the image acquisition function;

a surgical instrument tip detection function that detects a position of a tip portion of a surgical instrument in the image acquired by the image acquisition function using a surgical instrument detection model that has learned in advance a shape of the tip portion of the surgical instrument;

an organ damage determination function that determines whether the position of the tip portion detected by the surgical instrument tip detection function has reached the organ that is likely to be damaged during the surgery estimated by the organ area estimation function; and an organ damage notification function that notifies a surgeon of a possibility of organ damage when the organ damage determination function determines that the position of the tip portion has reached the estimated organ.

7. A surgery assisting system comprising:

an image acquisition system configured to acquire an image captured by an endoscope;

a surgical technique selection reception system configured to accept a selection of a surgical technique of a surgery;

an organ area estimation system configured to input the image acquired by the image acquisition system and identification information indicating the surgical technique accepted by the surgical technique selection reception system into an organ area estimation model that has learned in advance a relationship among identification information indicating the surgical technique of the surgery, the image captured by the endoscope during the surgery, and a position and range of an organ that is likely to be damaged during the surgery associated with the surgical technique in the image to estimate the position and range of the organ that is likely to be damaged during the surgery in the image acquired by the image acquisition system; and an estimated area display system configured to superimpose and display information indicating the position and range of the organ that is likely to be damaged during the surgery estimated by the organ area estimation system on the image acquired by the image acquisition system, wherein when the organ area estimation system estimates a position and range of each of a plurality of organs with a high probability of being damaged during the surgery in the image acquired by the image acquisition system, the estimation area display system displays information indicating the organs with a high probability of being damaged during the surgery estimated by the organ area estimation system by superimposing the information on the image acquired by the image acquisition system in different display forms, respectively.

8. The surgery assisting system according to claim 7, further comprising:

a surgical instrument tip detector that detects a position of a tip portion of a surgical instrument in the image acquired by the image acquisition system using a surgical instrument detection model that has learned in advance a shape of the tip portion of the surgical instrument;

a vascular detector that detects a position and range of a blood vessel in the image acquired by the image acquisition system;

a vascular injury determination system configured to determine whether the position of the tip portion detected by the surgical instrument tip detector has reached the blood vessel detected by the vascular detector; and a vascular injury notification system configured to notify a surgeon of a possibility of vascular injury when the vascular injury determination system determines that the position of the tip portion has reached the detected blood vessel.

9. The surgery assisting system according to claim 7, wherein the organ area estimation model learns in advance a form of movement associated with automaticity if an organ to be learned has automaticity, and if the organ with a high probability of being damaged during the surgery estimated by the organ area estimation system has automaticity, the estimated area display system superimposes and displays information indicating the organ with a high probability of being damaged during the surgery estimated by the organ area estimation system on the image acquired by the image acquisition system with the information highlighted in a predetermined form.

10. The surgery assisting system according to claim 7, further comprising:

an exposure degree determination system configured to determine an exposure degree of an organ with a high probability of being damaged during the surgery by comparing the position and range of the organ with a high probability of being damaged during the surgery estimated by the organ area estimation system with the image acquired by the image acquisition system, wherein the estimation area display system changes a display form of information indicating the organ that is likely to be damaged during the surgery estimated by the organ area estimation system in accordance with the exposure degree determined by the exposure degree determination system.

11. A surgery assisting method that causes a computer used in a surgery assisting system to perform:

an image acquisition step of acquiring an image captured by an endoscope;

a surgical technique selection reception step of accepting a selection of a surgical technique of a surgery;

an organ area estimation step of inputting the image acquired in the image acquisition step and identification information indicating the surgical technique accepted in the surgical technique selection reception step into an organ area estimation model that has learned in advance a relationship among identification information indicating the surgical technique of the surgery, the image captured by the endoscope during the surgery, and a position and range of an organ that is likely to be damaged during the surgery associated with the surgical technique in the image to estimate the position and range of the organ that is likely to be damaged during the surgery in the image acquired in the image acquisition step; and an estimated area display step of superimposing and displaying information indicating the position and range of the organ that is likely to be damaged during the surgery estimated in the organ area estimation step on the image acquired in the image acquisition step, wherein when the organ area estimation step estimates a position and range of each of a plurality of organs with a high probability of being damaged during the surgery in the image acquired in the image acquisition step, the estimated area display step displays information indicating the organs with a high probability of being damaged during the surgery estimated in the organ area estimation step by superimposing the information on the image acquired in the image acquisition step in different display forms, respectively.

12. A non-transitory computer readable medium storing therein a surgery assisting program that causes a computer used in a surgery assisting system to embody:

an image acquisition function that acquires an image captured by an endoscope;

a surgical technique selection reception function that accepts a selection of a surgical technique of a surgery;

an organ area estimation function that inputs the image acquired by the image acquisition function and identification information indicating the surgical technique accepted by the surgical technique selection reception function into an organ area estimation model that has learned in advance a relationship among identification information indicating the surgical technique of the surgery, the image captured by the endoscope during the surgery, and a position and range of an organ that is likely to be damaged during the surgery associated with the surgical technique in the image to estimate the position and range of the organ that is likely to be damaged during the surgery in the image acquired by the image acquisition function; and an estimated area display function that superimposes and displays information indicating the position and range of the organ that is likely to be damaged during the surgery estimated by the organ area estimation function on the image acquired by the image acquisition function, wherein when the organ area estimation function estimates a position and range of each of a plurality of organs with a high probability of being damaged during the surgery in the image acquired by the image acquisition function, the estimated area display function displays information indicating the organs with a high probability of being damaged during the surgery estimated by the organ area estimation function by superimposing the information on the image acquired by the image acquisition function in different display forms, respectively.

13. A surgery assisting system comprising:

an image acquisition system configured to acquire an image captured by an endoscope;

a surgical technique selection reception system configured to accept a selection of a surgical technique of a surgery;

an organ area estimation system configured to input the image acquired by the image acquisition system and identification information indicating the surgical technique accepted by the surgical technique selection reception system into an organ area estimation model that has learned in advance a relationship among identification information indicating the surgical technique of the surgery, the image captured by the endoscope during the surgery, and a position and range of an organ that is likely to be damaged during the surgery associated with the surgical technique in the image to estimate the position and range of the organ that is likely to be damaged during the surgery in the image acquired by the image acquisition system; and an estimated area display system configured to superimpose and display information indicating the position and range of the organ that is likely to be damaged during the surgery estimated by the organ area estimation system on the image acquired by the image acquisition system, wherein the image acquisition system acquires a plurality of consecutive images, and the organ area estimation system inputs the consecutive images acquired by the image acquisition system into the organ area estimation model to estimate a trajectory of a position and range of an organ with a high probability of being damaged during the surgery.

14. The surgery assisting system according to claim 13, further comprising:

a surgical instrument tip detector that detects a position of a tip portion of a surgical instrument in the image acquired by the image acquisition system using a surgical instrument detection model that has learned in advance a shape of the tip portion of the surgical instrument;

a vascular detector that detects a position and range of a blood vessel in the image acquired by the image acquisition system;

a vascular injury determination system configured to determine whether the position of the tip portion detected by the surgical instrument tip detector has reached the blood vessel detected by the vascular detector; and a vascular injury notification system configured to notify a surgeon of a possibility of vascular injury when the vascular injury determination system determines that the position of the tip portion has reached the detected blood vessel.

15. The surgery assisting system according to claim 13, wherein the organ area estimation model learns in advance a form of movement associated with automaticity if an organ to be learned has automaticity, and if the organ with a high probability of being damaged during the surgery estimated by the organ area estimation system has automaticity, the estimated area display system superimposes and displays information indicating the organ with a high probability of being damaged during the surgery estimated by the organ area estimation system on the image acquired by the image acquisition system with the information highlighted in a predetermined form.

16. The surgery assisting system according to claim 13, further comprising:

an exposure degree determination system configured to determine an exposure degree of an organ with a high probability of being damaged during the surgery by comparing the position and range of the organ with a high probability of being damaged during the surgery estimated by the organ area estimation system with the image acquired by the image acquisition system, wherein the estimation area display system changes a display form of information indicating the organ that is likely to be damaged during the surgery estimated by the organ area estimation system in accordance with the exposure degree determined by the exposure degree determination system.

17. A surgery assisting method that causes a computer used in a surgery assisting system to perform:

an image acquisition step of acquiring an image captured by an endoscope;

a surgical technique selection reception step of accepting a selection of a surgical technique of a surgery;

an organ area estimation step of inputting the image acquired in the image acquisition step and identification information indicating the surgical technique accepted in the surgical technique selection reception step into an organ area estimation model that has learned in advance a relationship among identification information indicating the surgical technique of the surgery, the image captured by the endoscope during the surgery, and a position and range of an organ that is likely to be damaged during the surgery associated with the surgical technique in the image to estimate the position and range of the organ that is likely to be damaged during the surgery in the image acquired in the image acquisition step; and an estimated area display step of superimposing and displaying information indicating the position and range of the organ that is likely to be damaged during the surgery estimated in the organ area estimation step on the image acquired in the image acquisition step, wherein the image acquisition step acquires a plurality of consecutive images, and the organ area estimation step inputs the consecutive images acquired by the image acquisition step into the organ area estimation model to estimate a trajectory of a position and range of an organ with a high probability of being damaged during the surgery.

18. A non-transitory computer readable medium storing therein a surgery assisting program that causes a computer used in a surgery assisting system to embody:

an image acquisition function that acquires an image captured by an endoscope;

a surgical technique selection reception function that accepts a selection of a surgical technique of a surgery;

an organ area estimation function that inputs the image acquired by the image acquisition function and identification information indicating the surgical technique accepted by the surgical technique selection reception function into an organ area estimation model that has learned in advance a relationship among identification information indicating the surgical technique of the surgery, the image captured by the endoscope during the surgery, and a position and range of an organ that is likely to be damaged during the surgery associated with the surgical technique in the image to estimate the position and range of the organ that is likely to be damaged during the surgery in the image acquired by the image acquisition function; and an estimated area display function that superimposes and displays information indicating the position and range of the organ that is likely to be damaged during the surgery estimated by the organ area estimation function on the image acquired by the image acquisition function, wherein the image acquisition function acquires a plurality of consecutive images, and the organ area estimation function inputs the consecutive images acquired by the image acquisition function into the organ area estimation model to estimate a trajectory of a position and range of an organ with a high probability of being damaged during the surgery.

* * * * *